United States Patent [19]

Brode, II et al.

[11] Patent Number: 4,663,159

[45] Date of Patent: May 5, 1987

[54] HYDROPHOBE SUBSTITUTED, WATER-SOLUBLE CATIONIC POLYSACCHARIDES

[75] Inventors: George L. Brode, II, Bridgewater; Russell L. Kreeger, Somerville; Errol D. Goddard, Haworth; Frederick M. Merritt, II, Belle Mead, all of N.J.; David B. Braun, Ridgefield, Conn.

[73] Assignee: Union Carbide Corporation, Danbury, Conn.

[21] Appl. No.: 697,241

[22] Filed: Feb. 1, 1985

[51] Int. Cl.$^4$ .......................... A61K 7/06; C08B 11/00
[52] U.S. Cl. ..................................... 424/70; 536/43; 536/90; 536/91; 514/844; 514/847
[58] Field of Search .................... 536/90; 424/47, 70; 514/844, 847

[56] References Cited

U.S. PATENT DOCUMENTS

| | | | |
|---|---|---|---|
| 3,472,840 | 10/1969 | Stone et al. | 536/31 |
| 4,001,394 | 1/1977 | Fogel et al. | 252/544 |
| 4,228,277 | 10/1980 | Landoll | 536/91 |
| 4,243,802 | 1/1981 | Landoll | 536/91 |

FOREIGN PATENT DOCUMENTS 0109074  5/1984  European Pat. Off. .
8228003  of 0000  Japan .

Primary Examiner—Johnnie R. Brown
Assistant Examiner—Elli Peselev
Attorney, Agent, or Firm—Henry H. Gibson

[57] ABSTRACT

Water-soluble, cationic polysaccharides, including quaternary nitrogen-containing cellulose ethers, containing hydrophobic substitution, are substantially water-soluble; provide aqueous solutions having enhanced viscosity, foaming and preferably improved surface properties; and possess utility in personal care, emulsions and cleansers.

39 Claims, No Drawings

HYDROPHOBE SUBSTITUTED, WATER-SOLUBLE CATIONIC POLYSACCHARIDES

BACKGROUND OF THE INVENTION

1. Field of the Invention

This invention relates to water-soluble, cationic polysaccharides, more particularly, to such polysaccharides, especially quaternary nitrogen-containing cellulose ethers, containing hydrophobic substitution, as well as their utility in aqueous systems and personal care applications.

2. Description of Background Information

Water-soluble, quaternary nitrogen-containing polysaccharides, such as the cellulose ether derivatives described in U.S. Pat. No. 3,472,840 (Stone et al.), are known to possess desirable properties, such as substantivity to many substrates, useful in a variety of applications. Such materials have found utility as flocculants, as pigment retention aids, in paper-making, as anti-static fibers and fabrics, as hand stiffeners for fabrics, in personal care formulations, in adhesives, in printing inks, and so on.

Quaternary nitrogen-containing polysaccharides, such as the cellulose ethers described in Stone et al., are relatively polar compounds due to the presence of the cationic substituents, i.e., the quaternary nitrogen, and absence of lipophilic groups. Such compounds are therefore of limited usefulness in their application to materials and systems which are relatively incompatible with such polar, ionic polymers. In particular, aromatic compounds, such as perfumes, which are lipophilic in character, are not readily retained by such ionic polysaccharides as the quaternary nitrogen-containing cellulose ethers in Stone et al.

Furthermore, cationic polysaccharides, including the cationic quaternary nitrogen-containing cellulose ethers in Stone et al., are sensitive to the presence of other ionic species, such as salts, which are typically found in various applications, such as ionic surfactants used in personal care solutions. The salt sensitivity of ionic polysaccharides has been demonstrated in a variety of ways. Salt addition to aqueous solutions of ionic polysaccharides will generally result in reduced viscosities of such solutions, probably due to interactions between the ionic substituents in the polysaccharide and the ionic species of salt in solution.

U.S. Pat. Nos. 4,228,277 (Landoll I) and 4,243,802 (Landoll II) describe nonionic cellulose ethers which have limited water-solubility. The disclosed nonionic cellulose ethers may contain a level of long-chain alkyl group substitution of from 0.2 wt. % up to a level which renders the cellulose ether either less than 1 wt. % soluble in water or water-insoluble. While some of the disclosed cellulose ethers provide highly viscous aqueous solutions, as well as a relatively high degree of surface activity, they are not substantive, as distinct from cationic polysaccharides in that nonionic polysaccharides do not interact with ionic substrates (such as keratinous material including hair, skin and the like).

European Patent Application Publication No. 109,074 (Massuda) describes polypeptides modified with long-chain tertiary amines to provide a cationic surfactant. The polypeptide is described as a surfactant providing substantivity to hair and skin as well as increased lubricity providing improved combing. Such protein surfactants have relatively low molecular weights, are substantially crystalline as compared with polysaccharides which are film-forming, substantially amorphous, high molecular weight polymers.

Japanese Patent Application Publication No. 82-28003 (Nakamura) pertains to quaternary nitrogen-containing cellulose ethers having benzyl or cinnamyl substituents useful in cosmetic applications. Such cellulose ethers containing benzyl or cinnamyl substituents provide compositions with increased protection from ultraviolet rays while maintaining cosmetic benefits characteristic of such quaternary nitrogen-containing cellulose ethers.

U.S. Pat. No. 4,001,394 (Fogel et al.) pertains to hair care compositions comprising an anionic or amphoteric detergent and a long-chain alkyl substituted, monomeric, quaternary ammonium compound, including saccharinate. It is disclosed that such hair care compositions provide improvements in cleansing activity and conditioning.

There is therefore a need, which has been long-standing since the development of the cationic, quaternary nitrogen-containing cellulose ethers in Stone et al., to provide quaternary nitrogen-containing polysaccharides exhibiting desirable substantivity and other properties significant for personal care applications, combined with enhanced compatibility with nonpolar materials but while retaining significant water-solubility. Such polysaccharides would have widespread utility to applications not heretofore obtained in the prior art.

SUMMARY OF THE INVENTION

The present invention pertains to water-soluble, cationic polysaccharides, particularly quaternary nitrogen-containing derivatives of cellulose ethers such as hydroxyethyl cellulose. The polysaccharides are represented by the overall structural formula:

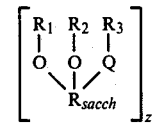

In Formula I:
Q is

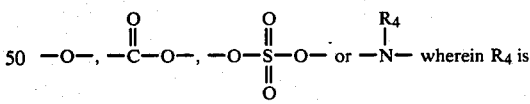

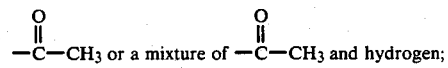

$R_{sacch}$ is the residue of a polysaccharide repeat unit;
z is from 50 to about 20,000; and
each $R_1$, $R_2$ and $R_3$ is individually represented by the substituent structural formula:

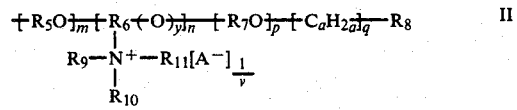

In Formula II:
A is an anion;

a is an integer of from 1 to about 3;

m is an integer of from 0 to about 6;

n is an integer of from 0 to about 3, provided that the level of cationic substitution, CS, defined by the average moles of quaternary nitrogen atoms per mole of polysaccharide repeat unit is greater than 0;

p is an integer of from 0 to about 6;

q is 0 or 1;

each $R_5$ and $R_7$ is individually ethylene, a propylene or a hydroxypropylene;

$R_6$ is a di- or trivalent, branched or straight chain, saturated or unsaturated hydrocarbon having from 2 to about 4 carbon atoms, provided there are at least two carbon atoms between the nitrogen atom and any oxygen atom;

$R_8$ is hydrogen, hydroxyl, $R_h$, carboxyl or alkali metal or amine salt thereof, provided that when q is 0 then $R_8$ is hydrogen or $R_h$;

each $R_9$, $R_{10}$ and $R_{11}$ is individually $R_h$, alkyl, aryl, aralkyl, alkaryl, cycloalkyl, alkoxyaryl or alkoxyalkyl, having at least two carbon atoms separating the oxygen atom in the alkoxyaryl or alkoxyalkyl group from the nitrogen atom;

$R_h$ is a hydrophobic group containing an alkyl group having at least 8 carbon atoms;

v is equal to the valence of A;

y is 0 or 1, provided that when y is 0 then p and q are 0 and $R_8$ is hydrogen;

with the proviso that the extent of hydrophobic group substitution, HS, defined by the average moles of said hydrophobic groups per mole of polysaccharide repeat unit is greater than 0.

Aqueous solutions and personal care products containing these polysaccharides are also described.

DETAILED DESCRIPTION OF THE INVENTION

The present invention is based on the discovery that novel, water-soluble, cationic polysaccharides containing hydrophobic group substituents, i.e., hydrophobes, may be prepared which possess a desirable combination of properties useful in a variety of applications, including personal care products. Such polysaccharides are substantially water-soluble; provide enhanced viscosification, foaming, and in a preferred embodiment, surface tension reduction properties, when in aqueous solution; and exhibit a balance of properties indicating desirable utility in personal care applications.

The hydrophobe substituted polysaccharides of this invention may be produced from readily available materials. Such polysaccharides are derived from naturally occurring polysaccharides, or those modified by etherification, which are quaternized with a nitrogen-containing compound and alkylated with a compound, including a nitrogen-containing compound, containing a hydrophobe.

Polysaccharide starting materials include the naturally occurring, biosynthesized and derivatized carbohydrate polymers or mixtures thereof. Such materials encompass high molecular weight polymers composed of monosaccharide units joined by glycosidic bonds. These materials include the entire starch and cellulose families; pectin; chitosan; chitin; the seaweed products such as agar and carrageenan; alginate; the natural gums such as guar, arabic and tragacanth; bio-derived gums such as xanthan; and the like. Preferred starting materials include cellulosics conventionally employed for the preparation of cellulose ethers, such as chemical cotton, cotton linters, wood pulp, alkali cellulose, and the like and ether derivatives of the same. Such cellulose ethers include hydroxyethyl cellulose, hydroxypropyl cellulose, methyl cellulose, carboxymethyl cellulose, carboxyethyl cellulose, hydroxypropyl methyl cellulose, hydroxyethyl methyl cellulose, hydroxyethyl carboxymethyl cellulose, and the like. A particularly preferred polysaccharide starting material is hydroxyethyl cellulose. The polysaccharide starting material possesses a molecular weight corresponding to the number of polysaccharide repeat units, usually from 50 up to about 20,000. The molecular weight of the polysaccharides may be varied through controlled degradation procedures known in the art.

Etherified polysaccharides may be obtained commercially or produced from the polysaccharide starting materials mentioned previously. Etherification involves reacting pendent hydroxyl groups on the polysaccharide backbone with an etherifying agent, or mixtures thereof, which contain functional groups reactive with such hydroxyl groups. Etherification may be conducted to enhance the water-solubility of the polysaccharides, e.g. by ethoxylation. Typical etherifying agents include lower alkylating agents such as dimethyl sulfate, diethyl sulfate, methyl chloride, methyl bromide, ethyl chloride, ethyl bromide or n-propyl chloride; hydroxy alkylating agents such as ethylene oxide, propylene oxide or glycidol; and carboxy alkylating agents such as monochloroacetic acid, sodium chloroacetate or chloropropionic acid.

The extent of etherification may be characterized by the average number of moles of substituents provided by the etherifying agent per mole of polysaccharide repeat unit, defined as molar substitution, hereinafter referred to as "MS".

The polysaccharide starting materials are provided with quaternary nitrogen-containing substituents through quaternization reactions. Quaternization may be achieved by reacting the polysaccharides with quaternizing agents which are quaternary ammonium salts, including mixtures thereof, to effect substitution of the polysaccharide chain with quaternary nitrogen-containing groups. Typical quaternary ammonium salts which can be utilized include quaternary nitrogen-containing halides, halohydrins and epoxides. The quaternary ammonium salt may contain hydrophobes. Exemplary ammonium salts include one or more of the following:

3-chloro-2-hydroxypropyl dimethyldodecyl ammonium chloride; 3-chloro-2-hydroxypropyl dimethyloctadecyl ammonium chloride; 3-chloro-2-hydroxypropyldimethyloctyl ammonium chloride;

3-chloro-2-hydroxypropyl trimethyl ammonium chloride; 2-chloroethyl trimethyl ammonium chloride; 2,3-epoxypropyl trimethyl ammonium chloride; and the like. Preferred quaternization agents include 3-chloro-2-hydroxypropyl trimethyl ammonium chloride; 3-chloro-2-hydroxypropyl dimethyldodecyl ammonium chloride; 3-chloro-2-hydroxypropyl dimethyltetradecyl ammonium chloride;

3-chloro-2-hydroxypropyl dimethylhexadecyl ammonium chloride; and 3-chloro-2-hydroxypropyl dimethyloctadecyl ammonium chloride.

Quaternization can also be achieved using a two-step synthesis of (1) aminating the polysaccharide by reaction with an aminating agent, such as an amine halide, halohydrin or epoxide, followed by (2) quaternizing the product of step (1) by reaction with quaternizing agent, or mixtures thereof, containing a functioning group which forms a salt with the amine. Preferred quaternizing agents include hydrophobe containing long chain alkyl halides, including those alkylating agent halides discussed below.

The extent of quaternization may be characterized by CS, as defined previously.

The polysaccharides are alkylated to provide the requisite hydrophobic substituents, i.e. hydrophobes in the polysaccharide. Such alkylation may be conducted in a separate reaction step, or may be combined in the etherification or quaternization reactions by incorporating hydrophobes into the etherifying or quaternizing agent, respectively. The hydrophobes may therefore be provided as substituents connected directly to the polysaccharide chain, the quaternary nitrogen or as part of the ether substituent. Alkylation is achieved by reacting alkylating agent, or mixtures thereof, containing at least one hydrophobe and functional group which is reactive (1) with the hydroxyl groups on the polysaccharide chain or ether substituents, or (2) with a tertiary nitrogen atom, producing a quaternary substituent, or (3) both.

The hydrophobes of this invention contain alkyl groups having at least 8, preferably from about 10 to about 24, and most preferably from about 10 or 12 to about 18 carbon atoms in the alkyl chain. The alkyl containing hydrophobe may be unsubstituted, i.e., simply a long chain alkyl group, or substituted with nonreactive groups such as aromatics, i.e., an aralkyl group. Typical alkylating agents reactive with the polysaccharide hydroxyl groups include halides, epoxides, isocyanates, carboxylic acids or acid halides. Typical alkylating agents reactive with the nitrogen atom include halides, epoxides and halohydrins.

Exemplary alkylating agents include dodecyl bromide, octadecyl chloride, 1,2-hexadeceneoxide, octadecanoic acid, and the like as well as the hydrophobe-containing quaternizing agents previously listed.

The extent of alkylation may be characterized by the HS as defined previously.

The etherification, quaternization and alkylation steps may be conducted in any order, or simultaneously, as well as repeated, to produce the desired substituted polysaccharides. Furthermore, as noted previously, one or more of the etherifying, quaternizing or alkylating agents may be combined to reduce the number of synthesis steps or to achieve different balances of various substituents. For example, hydrophobe substituted, cationic polysaccharides of this invention may be prepared (1) by etherification followed by combined quaternization/alkylation, optionally followed by further etherification and/or quaternization; (2) by simply combined quaternization/alkylation without any etherification; or any of numerous variations of such procedures.

The reaction procedures for providing the hydrophobe substituted, cationic polysaccharides of this invention follow standard reaction procedures established in the art.

Suitable reaction conditions for effecting etherification, when desired, are those conditions employed in the preparation of conventional polysaccharide derivatives, whether or not the etherification is effected before or after the quaternization or alkylation steps. Thus, the etherification may be conducted at temperatures from about 25° C. to about 125° C., preferably from about 45° C. to about 95° C., with or without the use of a diluent, and with a reaction time of from about 0.5 to about 10 hours or more, preferably from 1 to 4 hours. Alkaline catalysis is employed in all instances, with sodium hydroxide being the preferred catalyst. The amount of catalyst employed varies broadly, with the optimum amount depending on such factors as the particular ether being prepared, the amount of etherifying agent, the temperature, the reaction medium, and the like.

The quaternization reaction may be readily effected at temperatures of from about 5° C. to about 80° C., with preferred temperatures being in the range of from about 40° C. to about 65° C., for a time required to accomplish the reaction varying from about 0.5 to about 8 hours or longer, typically from about 1 to about 3 hours. Alkaline catalysts, such as sodium hydroxide, potassium hydroxide, lithium hydroxide, tetramethyl ammonium hydroxide, tetraethyl ammonium hydroxide, and the like, may be employed. The amount of catalyst utilized will depend upon whether the quaternizing agent employed is a halohydrin, epoxide, or halide, as well as upon the degree of quaternization desired. Where a quaternary halohydrin is employed, an amount of catalyst of from slightly more than 1 to 3 moles per mole of quaternary halohydrin is satisfactory, while when the quaternary epoxide is employed suitable amounts are from about 0.01 to about 2 moles per mole of quaternary epoxide. The proportion of quaternary ammonium salt to polysaccharide may be in the range of from about 0.01 to about 3 moles of quaternary ammonium salt per polysaccharide repeat unit, preferably from about 0.1 to about 2.5 moles per polysaccharide repeat unit. Quaternization of tertiary amines can be readily accomplished in an inert diluent, such as ethanol at reflux, with or without strong base catalyst, for about 2 to about 6 hours.

The alkylation step is usually conducted in an inert organic diluent in the presence of a caustic catalyst, such as alkali metal hydroxide. The reaction may be conducted at a temperature of from about 50° C. to about 115° C., preferably from about 70° C. to about 95° C., for a time sufficient to accomplish the alkylation reaction varying from about 0.5 to about 8 hours or longer, typically from about 1 to about 5 hours.

The etherification, quaternization and alkylation reactions are typically conducted in an inert organic diluent such as a lower aliphatic alcohol or ketone, or an aliphatic or aromatic hydrocarbon. Exemplary diluents include alkanols, such as isopropyl alcohol, tertiary-butyl alcohol or the like; ketones such as acetone or the like; ethers such as diethyl ether or the like; hydrocarbons, such as hexane, benzene, toluene or the like and other such materials known in the art. Some diluents, such as acetone, can provide for enhanced alkylation, i.e. increased HS, compared to other diluents under similar reaction conditions.

The polysaccharide product of the etherification, quaternization and/or alkylation steps is neutralized to a slightly acidic pH to provide a product stable in air. Any of a variety of acids known in the art for such purposes may be employed. The polysaccharide product may then be recovered, washed with inert solvents, and dried.

Typical adjuvants which may be present during the etherification, quaternization or alkylation steps include any processing aids as are known in the art such as surfactants including anionic or nonionic compounds such as sulfonates, carboxylates and ethoxylated aliphatic or aromatic hydrocarbons, or the like.

In a typical embodiment, the hydrophobe substituted, cationic polysaccharides of this present invention are produced as follows. Polysaccharide starting material, such as hydroxyethyl cellulose, in a diluent, such as acetone, is added to a reactor vessel equipped with a stirrer, nitrogen supply, condenser and addition funnels. The reactor is purged with nitrogen and a catalyst, such as sodium hydroxide, is added as an aqueous solution. After stirring, such as for about half an hour, an aqueous solution containing quaternizing agent, or combined quaternizing/alkylating agent, is added. The reaction mixture is heated, usually to around 55° C. and held at such temperature for a period of time to permit the quaternization and/or alkylation reaction to go to completion, usually for about 3 hours. If alkylation is required further, a solution containing alkylating agent is added under similar reaction conditions until the alkylation reaction is substantially complete. An acidification agent, such as glacial acetic acid, is added to the reaction mixture with stirring. The reaction solids are collected by filtration, are washed repeatedly by aqueous solvent, and are dried to yield hydrophobe substituted, cationic polysaccharide product. The product can be analyzed to determine the weight percent nitrogen content (% N), CS, HS and MS, using established procedures.

The hydrophobe substituted, cationic polysaccharides of this invention are represented by the overall structural formula:

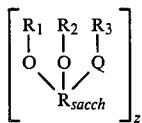

I

In Formula I, $R_{sacch}$ is the residue of a polysaccharide repeat unit derived from the polysaccharide starting materials previously described. The polysaccharide repeat unit may contain more than three "R" substituents for those polysaccharides which contain more than three reactive hydroxyl groups per repeat unit, as in for example xanthan gum which provides up to 11 hydroxyl groups per repeat unit available for etherification, quaternization or alkylation. $R_{sacch}$ is preferably the residue of an anhydroglucose repeat unit, particularly from cellulose.

The parameter Q in Formula I varies depending upon the particular polysaccharide being utilized. For example, Q is —O— when the particular polysaccharide comprises anhydroglucose repeat units such as in starch, cellulose or the like.
Similarly, Q is

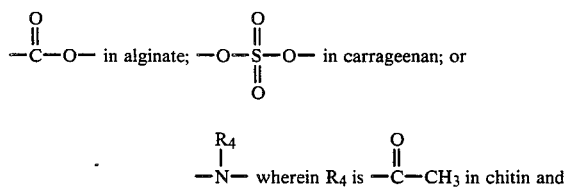

wherein $R_4$ is a mixture of hydrogen and

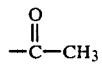

groups in chitosan. Q is preferably —O—, i.e. an oxygen atom.

The number of polysaccharide repeat units, defined by z in Formula I, is usually from about 50 to about 20,000, preferably from about 100 to about 6,000; and most preferably from about 250 to about 4,000. The corresponding molecular weights of the hydrophobe substituted, cationic polysaccharide will usually range from several thousand up to several million.

The $R_1$, $R_2$ and $R_3$ substituents in Formula I are either hydrogen, when representing unreacted hydroxyl groups of the polysaccharide, or those substituents provided by etherification, quaternization and/or alkylation. Each $R_1$, $R_2$ and $R_3$ is individually represented by the substituent structural formula:

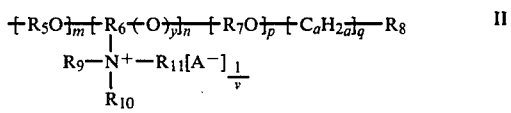

II

In Formula II, A is an anion, including mixtures of anions. Exemplary anions include inorganic anions such as chloride, bromide, iodide, sulfate, methylsulfate, sulfonate, nitrate, phosphate, and the like; and organic anions such as acetate, and the like. Monovalent anions are preferred, particularly halides, and especially chloride. The anions are typically provided as the residue of the quaternary ammonium salts used as quaternizing agents, or by ion exchange techniques.

The alkylene substituent defined by a in Formula II, contains from 1 to about 3 carbon atoms such that a is an integer having a value of from 1 to about 3.

The extent of etherification due to oxyalkylene substituents, as defined by m and p in Formula II, ranges from 0 to about 6 oxyalkylene groups each, i.e. m is an integer of from 0 to about 6 and p is an integer of from 0 to about 6. The additional extent of etherification, as defined by q in Formula II, depends upon the absence or presence of the alkylene group, i.e. $C_aH_{2a}$, such that q is 0 or 1, preferably 0.

The total extent of etherification, as measured in terms of MS as discussed previously, is usually greater than 0, preferably from about 1.2 to about 4.5, and most preferably from about 1.8 to about 3.6.

The number of quaternary nitrogen atoms per substituent, defined by n in Formula II, is from 0 to about 3, i.e. n is an integer of from 0 to about 3. The extent of quaternization, characterized as CS as discussed previously, is greater than 0, preferably less than 1 and most preferably from about 0.01 to about 0.6.

Each $R_5$ and $R_7$ in Formula II, defining the oxyalkylene substituent, is individually an ethylene (providing oxyethylene), a propylene (providing oxypropylene) or a hydroxypropylene (providing hydroxy substituted oxypropylene) unit. $R_5$ and $R_7$ are preferably ethylene or isopropylene, and most preferably ethylene.

The segment connecting the quaternary nitrogen to the polysaccharide molecule, defined as $R_6$ in Formula II, is a di- or a trivalent, branched or straight chain, saturated or unsaturated hydrocarbon having from 2 to about 4 carbon atoms, provided that there are at least 2 carbon atoms between the nitrogen atom and any oxygen atom, such as in the ether substituent or polysaccharide residue. $R_6$ can be ethylene, a $C_3$ hydrocarbon group, or $-CH_2CH=CHCH_2-$, and most preferably is

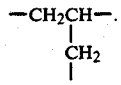

$R_8$ in Formula II is hydrogen, hydroxyl, $R_h$ as hereinafter defined, carboxyl or alkali metal or amine carboxylate, provided that when q is 0 then $R_8$ is hydrogen or $R_h$. $R_8$ is preferably hydrogen or $R_h$. When $R_8$ is hydrogen and m, n, p and q are all 0 the substituent structural formula provides an unsubstituted polysaccharide hydroxyl group.

The nitrogen substituents, defined by $R_9$, $R_{10}$ and $R_{11}$ in Formula II, are each individually $R_h$, alkyl, aryl, aralkyl, alkaryl, cycloalkyl, alkoxyalkyl or alkoxyaryl. If an alkoxyalkyl or alkoxyaryl substituent is provided, at least two carbon atoms separate the substituent oxygen atom from the nitrogen atom. Nitrogen substituents free of hydrophobes include: lower alkyls having from 1 to about 3 carbon atoms, such as methyl, or ethyl; aryls such as phenyl; aralkyls such as benzyl; and the like. Preferably at least two nitrogen substituents of each repeat unit are methyl, and the remaining substituent is $R_h$ or a mixture of $R_h$ and methyl among the nitrogen-containing repeat units in the polysaccharide molecule.

The hydrophobe, defined by $R_h$ in Formula II, contains a long chain alkyl group having at least 8 carbon atoms, preferably from about 10 to about 24 carbon atoms and most preferably from about 10 or 12 to about 18 carbon atoms. Hydrophobes containing alkyl groups which have less than 8 carbon atoms or aryl groups will generally not provide sufficient hydrophobic substitution to the quaternary nitrogen-containing polysaccharides to produce the superior combination of properties exhibitied by the hydrophobe substituted polysaccharides of this invention.

The polysaccharides of this invention, in addition to possessing substantial water-solubility, contain hydrophobes comprised of 8 or more alkyl carbon atoms in an amount sufficient to provide enhanced viscosification, foaming, and preferably surface tension lowering, of aqueous solutions containing the polysaccharides, as well as significant personal care utility. Preferred polysaccharides of this invention can provide significant personal care utility even at the expense of providing only modest enhancement in viscosity, foaming or surface tension properties.

$R_h$ may be attached directly to the quaternary nitrogen when present as $R_9$, $R_{10}$ or $R_{11}$; to the ether substituents as $R_8$; and/or directly to the polysaccharide residue as $R_8$ when m, n, p and q are all 0. The hydrophobes may be provided at any or all of these locations, in the same or different repeat units within the polysaccharide molecule.

$R_h$ may also contain a connecting segment between the alkyl and the ether oxygen atom depending upon the functional group contained in the alkylating agent used to connect the alkyl group to the polysaccharide. For example, $R_h$ may be: an alkyl group when an alkyl halide is the alkylating agent; an α-hydroxyalkyl group when an epoxide is the alkylating agent; a urethane alkyl group when an isocyanate is the alkylating agent; an acyl alkyl group when the alkylating agent is a carboxylic acid or acyl halide; and so on. $R_h$ is preferably a long chain alkyl group bonded directly to an oxygen atom or most preferably, to the quaternary nitrogen atom.

The valence of anion A, defined as v in Formula II, is an integer, preferably 1.

The absence or presence of the ether oxygen in the quaternary nitrogen substituent is defined by y in Formula II, i.e., y is 0 or 1, respectively, provided that in the absence of further ether substitution, i.e. when n is greater than 0 and y is 0, then p and q are 0 and $R_8$ is hydrogen. Preferably y is 1.

The extent of hydrophobe substitution, i.e. HS as defined previously, is greater than 0, preferably less than 1, and most preferably from about 0.01 to about 0.6.

Illustrative of some of the numerous possible substituents for an individual polysaccharide repeat unit include the following:

$-H$; $-CH_3$; $-C_{16}H_{33}$; $-CH_2CH_2OH$; $-CH_2CH_2CH_3$;
$-CH_2COOH$; $-CH_2COO^-Na^+$;
$-CH_2CH_2OCH_2CH_2OCH_2CH_2OH$;

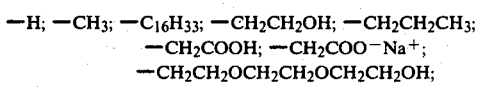

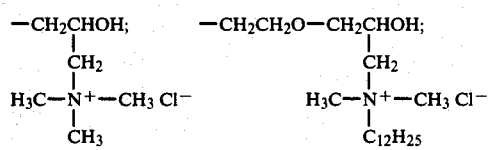

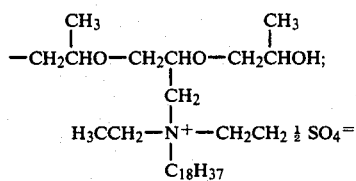

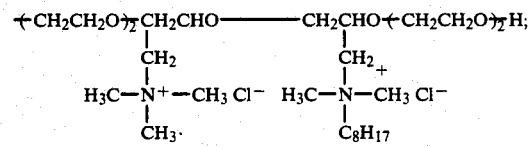

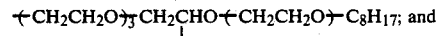

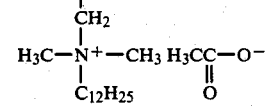

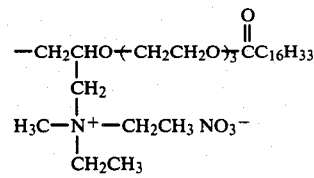

In a preferred embodiment, the hydrophobe substituted, cationic polysaccharide is a hydroxyethyl cellulose represented by the overall structural formula:

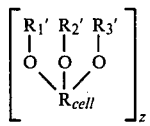

wherein:
$R_{cell}$ is the residue of an anhydroglucose repeat unit; z is from 50 to about 20,000; and
each $R_1'$, $R_2'$ and $R_3'$ is individually represented by the substituent structural formula:

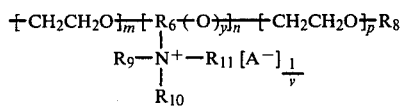

wherein:
A, m, n, p, $R_6$, $R_8$, $R_9$, $R_{10}$, $R_{11}$, v, y, $R_h$, CS and HS are as previously defined. The extent of ethoxylation in Formula IV, in terms of MS as previously defined, is preferably from about 1.2 to about 4.5, and most preferably from about 1.8 to about 3.6.

Chemical analysis to determine the structure of the hydrophobe substituted, cationic polysaccharides of this invention may be conducted using standard procedures known in the art, such as by nuclear magnetic resonance, i.e. "NMR" proton and $C_{13}$ analysis, gel permeation chromatography, active chloride/chlorined analyses and mass spectrometry. For example, the HS as discussed previously, of hydrophobe substituted, cationic polysaccharides produced by alkylating tertiary amine substituted polysaccharides can be analyzed by proton NMR spectroscopy by comparing the intensity of protons of the nitrogen substituents free of hydrophobes to the hydrophobe proton intensity. The molar ratio of unreacted tertiary amine to quaternary amine can then be calculated. In another procedure, CS can be calculated based on a percent nitrogen content determined by Kjeldahl nitrogen analysis combined with NMR proton analysis comparing the extent of hydrophobe substituted to nonhydrophobe substituted quaternary nitrogen.

As a class the hydrophobe substituted, cationic polysaccharides of this invention possess a desirable balance of properties. These desirable properties are demonstrated by analyzing aqueous solutions containing the polysaccharide.

The hydrophobe substituted, cationic polysaccharides of this invention are substantially water-soluble. Such water-solubility in the context of this invention is defined as the ability of substantial amounts, usually at least 1 to 2 weight percent, of the polysaccharide to dissolve in distilled water. Preferably, clear solutions are provided having little or no insolubles in 2 wt. % aqueous solution. Hydrophobe substituted, cationic polysaccharides provide increased water-solubility when compared to corresponding hydrophobe substituted, nonionic polysaccharides as in the prior art. The hydrophobe substituted, cationic polysaccharides of this invention can therefore achieve higher hydrophobe substitution levels without loss of water-solubility.

The substantial water-solubility of the hydrophobe substituted, cationic polysaccharides of this invention represents a balance between the hydrophilic portions of the polysaccharide molecule, such as provided by the cationic quaternary nitrogen-containing and oxyalkylene substituents, and the hydrophobic portions, such as the hydrophobes. To the extent that increased hydrophobe content limits water-solubility, a corresponding increase in hydrophilic substituents can be provided such that the polysaccharide retains substantial water-solubility.

The hydrophobe substituted, cationic polysaccharides of this invention are cationic usually due to the presence of quaternary nitrogen. Additional positively or negatively charged ionic groups may be present, such as carboxylate in carboxymethyl cellulose, providing the possibility for amphoteric structures. The quaternary nitrogen may be partially or completely replaced with other cationed substituents such as sulfonium, i.e.

or phosphonium, i.e.

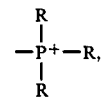

wherein each R group is individually hydrocarbyl or $R_h$ as described previously for $R_9$, $R_{10}$ and $R_{11}$, to provide hydrophobe substituted, cationic polysaccharides contemplated as within the scope of this invention. Polysaccharides containing quaternary nitrogen as the only cationic species present are preferred. A proportion of the nitrogen substituents may be present in the polysaccharide molecule in their corresponding nonquaternized, tertiary amine form as provided by the partial quaternization of amine substituents on the polysaccharide.

The viscosity of aqueous solutions containing the hydrophobe substituted, cationic polysaccharides is influenced by variations in the polysaccharide structure such as: molecular weight, i.e. z; the extent of quaternization, i.e. CS; the extent of etherification, i.e., MS; as well as other factors in solution including the presence of ions, such as by salt or surfactant addition.

The hydrophobe substituted, cationic polysaccharides of this invention provide enhanced viscosification of aqueous solutions containing the polysaccharide. The extent of viscosity enhancement provided by the hydrophobe substituted, cationic polysaccharides is based upon the hydrophobe content and depends upon the extent of the alkylation, i.e., HS, as well as the length of the long chain alkyl group in the hydrophobe.

Viscosity enhancement from increased hydrophobe content may be due to intermolecular association of individual polysaccharide molecules through the hydrophobes to form polymeric networks in solution. Support for this association can be seen in the rheology of the aqueous solutions. At relatively low shear rates up to 12 reciprocal secs, the solution exhibit only mild pseudoplasticity at higher viscosities and near Newtonian behavior at lower viscosities, but at shear rates of 200 reciprocal secs the viscosity drops to very low values. This non-linear shear thinning behavior is consistent with the formation of intermolecular bridges by the hydrophobes. Increased cationic substitution by quaternary nitrogen substituents which do not contain hydrophobes causes a reduction in the solution viscosity at a constant HS. It is believed that the increased cationic repulsion between molecules inhibits the formation of hydrophobe bridging resulting in a breakdown in the polymer network in solution.

Through selection and optimization of the various hydrophobe and/or non-hydrophobe related structural parameters influencing viscosification, hydrophobe substituted, cationic polysaccharides of this invention can be produced which provide a desired level of viscosity increase, within a potentially wide range of values. Aqueous solutions containing 2 wt. % concentrations of hydrophobe substituted, cationic polysaccharides of this invention will usually have a Brookfield viscosity, at 25° C., of at least 20 cps, preferably from about 25 cps to about 500,000 cps, and most preferably from about 50 cps to about 200,000 cps, depending upon the molecular weight of the polysaccharide.

In an embodiment of this invention, hydrophobe substituted, cationic polysaccharides provide increases in the viscosity of aqueous solutions containing increased ionic content, such as by adding an effective viscosifying amount of salt such as sodium chloride, or other halides, nitrates, sulfates or the like. This property directly contrasts the effect salt addition has on the viscosity provided by ionic polysaccharides of the prior art, for which salt addition to an aqueous solution would be expected to cause a collapse of the polymer chain thereby reducing hydrodynamic volume and, consequently, the solution viscosity.

The hydrophobe substituted, cationic polysaccharides of this invention provide improved surface properties to aqueous solutions containing such polysaccharides. To understand the significance of these improved surface properties the following explanation is provided.

As is well known to those skilled in the art, work is required to extend the surface of a liquid. This property is formally expressed by the surface tension parameter, which represents the work required to extend the surface by unit area. In metric units surface tension is expressed in ergs per square centimeter, or the equivalent unit dynes per centimeter, i.e. dyne/cm. Water, which is a strongly bonded liquid, has the comparatively high surface tension at room temperature of 72 dyne/cm. A typical hydrocarbon, such as octane, which is only weakly bonded, has a low value of 18 dyne/cm. Surfactants, such as those used in commercial detergents, by a process of adsorption, i.e. migration to the water surface, are able to reduce the surface tension of water considerably such as to 40 dyne/cm or lower. Conventional water-soluble polymers can also reduce the surface tension of water, but the extent of lowering is much less than with surfactants and seldom are surface tension values less than 45 dyne/cm encountered for such solutions, i.e. polymers are generally less surface active than surfactants.

Surface active material can migrate to and modify the property of a water surface to which it migrates. Such a surface of water can be formed when the second phase is air, a second liquid such as oil, or a solid, such as glass, keratin, including hair and skin, and so on. In the latter case when the water is removed, e.g. by drying or rinsing, it may be found that some of the surface active material, especially if polymeric, which has adsorbed to the water/solid surface is retained at the solid surface. This retention is known as substantivity and in this way the material can alter the surface properties of the particular solid contacted. The ionic character of surface active material, including polymerics, can influence the extent of substantivity, particularly with regard to ionic substrates, presumably due to the electrostatic interaction between the material and substrate. For example, nonionic polysaccharides do not exhibit significant substantivity to keratinous substrates which have negative charge whereas, cationic polysaccharides exhibit substantivity to keratinous substrates.

One possible consequence of the adsorption of surfactants or polymers leading to a lowering of surface tension of water, i.e. making it easier to extend the surface of the water, is the potential for generating foams of these solutions. Pure liquids, such as water, do not foam by themselves. However, foaming, and the extent to which it is retained, is not a simple function of the degree of lowering of the surface tension but depends on the specific nature of the surfactant or polymer.

There are various ways of assessing the foaming characteristics of solutions. A simple procedure is to introduce a given volume of solution into a volumetric cylinder, leaving a constant volume of air in it, cap the cylinder, and then shake it by hand vigorously for a certain period of time, e.g. for 30 seconds. Foaming may be assessed by the initial height of the foam or, more preferably, by measuring the persistence or stability of the foam with time. The term "foaming" as used in the context of this invention therefore describes the ability to form foam as well as retain foam over time.

The hydrophobe substituted, cationic polysaccharides of this invention provide for enhanced foaming of aqueous solutions containing the polysaccharide.

In a preferred embodiment, particular hydrophobe substituted, cationic polysaccharides of this invention, such as those based on hydroxyethyl cellulose, provide enhanced, i.e., increased, surface pressure values to aqueous solutions containing the polysaccharide. The significance of this property can best be understood in the following context.

When dissolved in water, the molecules of a surfactant or a surface active polymer will migrate to the surfaces which bound the water solution. For a solution in an open vessel, these water surfaces are the top one against air while the sides and the bottom one are against the material of the containing vessel, such as against glass. The water surface with air is that one involved in measurements of surface tension, as previously described. The process of molecules migrating to, and locating in, the surface is known as adsorption. Generally, the saturation or equilibrium amount of solute in the surface is very small and corresponds to a layer of solute only one molecule thick, i.e., a monolayer.

There is a technique for analyzing surface tension well known to surface chemists named the Langmuir-Adam film balance method. This technique is, for example, described in *The Physics and Chemistry of Surfaces,* by N. K. Adam, Oxford University Press, 1933. In this technique, a water surface on which there is a monolayer of solute, is subjected to a two-dimensional compression in which the original area available to the surfactant layer is continually decreased. Generally, with the solute being soluble, the monolayer overcomes this increased molecular crowding by releasing some of its molecules back into the solution. Thus, for surfactants which are comparatively small molecules, this release or desorption process is very rapid and the surface tension of the solution, which depends on the surface concentration of the surfactant, will scarcely change on two dimensional compression.

The situation with surface active polymers, which are comparatively large molecules, is very different. In their case, the molecules in the absorbed monolayer are sluggish in desorption. When such a layer is subjected to two-dimensional compression, there results an increase in the two-dimensional surface concentration, and the surface tension of the compressed film, as measured with the Langmuir-Adam film balance, will decrease. Thus, another measure of the surface activity of the polymer is provided, namely the "compressed surface tension".

In listing these values it is convenient to use another parameter, characterized as surface pressure, $\pi$. Surface pressure is defined as the difference between the surface tension of pure water, i.e. $\gamma_{H_2O}$, and the surface tension of an aqueous solution with a surface containing a monolayer of surfactive molecules, i.e. $\gamma$. Thus $\pi = \gamma_{H_2O} - \gamma$, such that the lower the surface tension of the solution, the greater the surface pressure. With compression of the surface, as described above, there is an analogous parameter, the "compressed surface pressure", $\pi_c$, defined by the equation, $\pi_c = \gamma_{H_2O} - \gamma_c$ wherein $\gamma_c$ is the compressed surface tension of a solution with a surface containing a compressed monolayer of surfactive molecules. These afford a measure of the inherent surface activity of a polymer, significant for describing a substance's ability to modify substrates, such as keratin, to which an aqueous solution of the polymer is applied.

Preferred hydroprobe substituted, cationic polysaccharides of this invention provide enhanced surface pressures of aqueous solutions containing the polysaccharide. This property is much more pronounced for polysaccharides which, prior to hydroprobe substitution, provide only minimal surface activity.

In one embodiment of this invention, hydroprobe substituted, cationic polysaccharides have been found to provide a capacity for solubilizing lipophilic compounds, such as oil soluble dyes.

In another embodiment of this invention, hydrophobe substituted, cationic polysaccharides when applied to keratinous substrates have been found to increase the surface hydrophobicity of the keratin as compared with such properties of corresponding polysaccharides free of hydrophobe substitution. This property can be best described in the following context.

A sensitive measure of the hydrophilic/hydrophobic character of a smooth solid surface is the contact angle ($\theta$) which a drop of liquid, such as water, makes with said surface when the drop is placed on it. For example, water forms a very low contact angle with a hydrophilic surface such as very clean glass ($\theta$ close to zero). By contrast, water forms a much higher contact angle with hydrophobic surfaces such as fatty or waxy surfaces, like paraffin wax ($\theta$ around 100°). By this means one can measure the hydrophilicity or hydrophobicity of a solid surface very easily.

Solid surfaces, such as polished keratin, a model for human skin or hair, give a higher contact angle with water when various hydrophobe substituted polysaccharides of this invention are adsorbed onto the surface than the contact angle using corresponding polysaccharides without hydrophobes.

On balance, the hydrophobe substituted, cationic polysaccharides of this invention provide a desirable combination of properties, including utility in personal care applications. Enhanced solution viscosity, emulsification, foaming and surface pressure properties combined with the substantivity and desirable cosmetic properties exhibited by cationic quaternary nitrogen-containing polysaccharides make the hydrophobe substituted, cationic polysaccharides of this invention particularly suitable to an expanded number of cosmetic and noncosmetic applications.

The hydrophobe substituted, cationic polysaccharides of this invention may be used in compositions for the retention of oils, perfumes, emollients and the like; in hair and skin care compositions including water-in-oil or oil-in-water emulsions, lotions, creams, soaps, cleansers, sunscreens, shampoos, rinses, conditioners, antidandruff aids; as carriers for active agents in, for example, internal drugs; in dispersants; as flow control aids in flocculants; as thickeners; in antistatic softeners; in textile applications; or as topically active agents to various substrates such as metal, glass and so on.

Compositions containing the hydrophobe substituted, cationic modified polysaccharides of this invention may contain additives or adjuvants consistent with the prior art teachings in such end use applications. For example, in personal care applications the composition may contain solvent, such as water or alcohol; and surfactants, including anionic or nonionic compounds such as sulfonates, carboxylates and ethoxylated aliphatic or aromatic hydrocarbons, or the like.

The hydrophobe substituted, cationic polysaccharides, when compared with a polysaccharide having essentially the same structure but which is free of hydrophobe substitution, provide significantly increased viscosity and foaming, and preferably higher surface pressure, to aqueous solutions of the polysaccharides. For purposes of comparison in this invention, polysaccharides free of hydrophobe substitution are those structures otherwise represented by Formulas I-IV but wherein the $R_h$ groups are replaced with substituents of relatively limited hydrophobicity such as: hydrogen; lower alkyl groups including methyl, ethyl; aryl groups including phenyl, benzyl, cinnamyl; and so on. The quaternary nitrogen-containing polysaccharides in the prior art, such as described in Stone et al, describe polysaccharide embodiments with quaternary nitrogen and etherified substituents which do not impart significant hydrophobic character to the polysaccharide.

Hydrophobe substituted, cationic polysaccharides of this invention as a class generally provide an aqueous solution viscosity, at a 2 wt. % polysaccharide content at 25° C., which is in excess of about 115%, preferably in excess of 200%, and most preferably from about 300% to about 100,000%, as compared with a similar aqueous solution of polysaccharide having essentially the same structure but which is free of the hydrophobic substitution.

Hydrophobe substituted, cationic polysaccharides of this invention as a class generally provided aqueous solutions with significant foam 24 hrs after agitation. By comparison, cationic or nonionic polysaccharides having essentially the same structure but which are free of hydrophobic substitution provide aqueous solutions having little or no foaming after 24 hours.

Preferred hydrophobe substituted, cationic polysaccharides of this invention as a class generally provide aqueous solutions with a surface pressure or a compressed surface pressure, under such experimental conditions as set forth below, which are in excess of about 110%, preferably in excess of about 120%, and most preferably from about 125% to about 300%, as compared with a polysaccharide having essentially the same structure but which is free of the hydrophobic substitution.

This invention is further illustrated in the following examples, which are merely representative of various embodiments within the scope of the claims.

EXAMPLES

The chemical designations and abbreviations used in the examples are defined as follows:

| DESIGNATION | DESCRIPTION |
|---|---|
| Alginate | Sodium alginate having a 2 wt. % Brookfield viscosity of 250 cp, distributed by Sigma Chemical Co. |
| $C_8ACl$ | 3-chloro-2-hydroxypropyl dimethyloctyl ammonium chloride. |
| $C_{10}ACl$ | 3-chloro-2-hydroxypropyl dimethyldecyl ammonium chloride. |
| $C_{12}ACl$ | 3-chloro-2-hydroxypropyl dimethyldodecyl ammonium chloride, distributed under the tradename QUAB ™ 342 by Degussa Chemical Co. |
| $C_{18}ACl$ | 3-chloro-2-hydroxypropyl dimethyloctadecyl ammonium chloride, distributed under the tradename QUAB ™ 426 by Degussa Chemical Co. |
| $C_{10}Br$ | Decyl bromide |
| $C_{12}Br$ | Dodecyl bromide |
| $C_{12}Cl$ | Dodecyl chloride |
| CDBACl | 3-chloro-2-hydroxypropyl dimethylbenzyl ammonium chloride, distributed under the tradename Benzyl-Reagens-D-CFZ ™ by Kay-Fries, Inc. |
| Cell | Cellulose cotton linters. |
| Chitosan | Chitosan, (about 60% deacetylated) having a wt. % Brookfield viscosity of 275 cps. in 0.7% acetic acid, distributed by Bioshell Co. |
| $ClAc^-Na^+$ | Sodium salt of chloroacetic acid |
| CMC | Carboxymethyl cellulose having a degree of substitution of about 0.9 and a 2 wt. % Brookfield viscosity range of 100–200 cps. distributed under the tradename Cellulose Gum ™ by Hercules, Inc. |
| CTACl | 3-chloro-2-hydroxypropyl trimethyl ammonium chloride distributed under the tradename Quaternium ™ 188 by Dow Chemical Co. |
| CTEACl | 3-chloro-2-hydroxypropyl triethyl ammonium chloride |
| DACl | Dimethylaminoethyl chloride |
| DHPC | 2,3-Dihydroxypropyl cellulose, as described in West German Patent Application Publication No. 3,301,667 (Engelskirchen et al.). |
| EO | Ethylene oxide |
| Gly | Glycidol |
| $HEC_{high\ MW}$ | Hydroxyethyl cellulose of relatively high molecular weight, providing a 2 wt. % Brookfield viscosity within 300–500 cps, and having an MS of about 2. |
| $HEC_{low\ MW}$ | Hydroxyethyl cellulose of relatively low molecular weight, providing a 2 wt. % Brookfield viscosity of about 23 cps and having an MS of about 2. |
| $HEC_{mid\ MW}$ | Hydroxyethyl cellulose of relatively moderate molecular weight, providing a 2 wt. % Brookfield viscosity of about 115 cps, and having and MS of about 2. |
| HEHPC | Hydroxyethyl hydroxypropyl cellulose distributed under the tradename Natrovis ® by Hercules Chemical Co., degraded to a 2 wt. % Brookfield viscosity of 54 cps. |
| HPMC | Hydroxypropyl methyl cellulose a methyl MS of 1.12–1.64 and a hydroxypropyl MS of 0.10–0.33 having a 2 wt. % Brookfield viscosity of 86 cps, distributed under the trade name METHOCEL ™ K100LV by Dow Chemical Co. |
| HSHEC | Hydrophobe substituted HEC having a 2 wt. % Brookfield viscosity of 2,210 cps, distributed under the tradename WSP-D-330 ™ by Hercules, Inc. |
| iso-$C_3$ | $-CH_2CH-$ <br> $\quad\quad\ \ |$ <br> $\quad\quad\ \ CH_2$ <br> $\quad\quad\ \ |$ |
| MC | Methyl cellulose having an MS of about 1.8 and a 2 wt. % Brookfield viscosity of 392 cps, distributed under the tradename METHOCEL ® A4C by Dow. |
| MCl | Methyl chloride |
| PO | Propylene oxide |
| QNHEC | Quaternary nitrogen-containing hydroxyethyl cellulose having a 2 wt. % Brookfield viscosity of 456 cps and about 1.8 wt. % N. |

The following test procedures describe the hydrophobe substituted, cationic polysaccharides of this invention, in terms as described above, and define the performance tests used in evaluating the polysaccharides.

CS: The extent of cationic substitution is calculated using the following relationship:

$$CS = \frac{\% N \cdot MW_P}{100 \cdot AW_N - \% N \cdot MW_{NS}}$$

wherein:

$AW_N$ is the atomic weight of nitrogen, i.e. 14;

$MW_P$ is the average molecular weight of the polysaccharide repeat unit prior to quaternization;

$MW_{NS}$ is the molecular weight of the nitrogen-containing substituent; and

% N is the weight percent of nitrogen as determined by the Dohrmann or Kjeldahl methods.

Foaming, $\phi$: Foaming is measured by introducing 30 ml of a 0.1 wt. % solution of the polysaccharide into a 100 ml volumetric cylinder, which is shaken vigorously for thirty seconds followed by measured foam volume in ml, initially and after standing for up to twenty-four hours.

Hair treatment: A one gram, 10-inch tress of commercially available virgin brown hair is treated with one gram of a 1 wt. % polysaccharide solution in water solvent with or without surfactant. The tress is attached to a board while still wet and tested for wet feel and appearance. After drying with a hair dryer, the tress is tested for dry appearance. Negative attributes including greasiness, stickiness, dryness, flakiness, lack of sheen and lack of slip are evaluated. Positive attributes of sheen, softness and slip are evaluated.

HS: The extent of hydrophobe substitution is calculated from the following relationship:

$$HS = CS_h + MS_h$$

wherein:

$CS_h$ is the contribution to CS due to the presence of hydrophobe containing quaternary nitrogen-containing substituents; and $MS_h$ is the contribution to MS due to the presence of hydrophobe-containing ether substituents. When all hydrophobic substitution is provided through quaternization then $HS = CS_h$; and when all such quaternization is combined with alkylation then $HS = CS$. When $HS = CS_h = CS$, the HS is calculated based on the weight percent of (hydrophobe-containing) nitrogen.

MS: The extent of molar substitution is determined analytically by the well known Zeisel-Morgan method used for ether substituted polysaccharides.

Nitrogen content, %N: The average weight percent of nitrogen per polysaccharide repeat unit is determined analytically by the standard Dohrmann or Kjeldahl methods.

Surface pressure, $\pi$: Surface pressure is determined using the previously identified Langmuir-Adam film balance procedures. A trough of fused silica which is 15 cm long by 9 cm wide by 2 cm deep, having a flat, paraffined waxed upper rim, is filled with 0.01 wt. % polysaccharide aqueous solution and the surface two dimensionally swept to remove contaminants. Following established techniques, the initial surfaced tension, $\gamma_0$, is measured and then measured again after aging for three hours, $\gamma_3$, to enable polysaccharide molecules, present in dilute solution, to adsorb at the surface. The surface is subjected to a three-fold reduction in surface area by 2 dimensional compression with a paraffin wax coated glass slide moving along the flat rim of the trough and the compressed surface tension, $\gamma_c$, is then measured. As discussed previously, the surface pressures, $\pi_0$, $\pi_3$ and compressed surface pressure, $\pi_c$, are then calculated.

Viscosity, $\eta$: Viscosity is measured using Cannon-Fenske or Brookfield LVT viscometers, based on an aqueous solution of 2 wt. % polysaccharide at 25° C., unless stated otherwise.

Water contact angle, $\theta$: Water contact angle is determined using a piece of polished keratin which is 10 cm long by 2 cm wide by 0.5 cm deep, which is treated by immersion for 30 minutes in an aqueous solution of 0.5 wt. % polysaccharide, followed by rinsing with water and then air drying. The average value of the water contact angle is then determined from several measurements.

EXAMPLE 1

Polysaccharide Preparation

The runs in this example detail the preparation and structure of various hydrophobe substituted, cationic polysaccharides of this invention and corresponding or similar polysaccharides free of hydrophobe substitution, i.e. controls.

Table I summarizes the preparation of hydrophobe substituted, cationic polysaccharides, as well as control polysaccharides free of hydrophobe substitution. Table I lists the various reactants, such as the polysaccharide starting material, and the etherification, quaternization and alkylation agents. The order of substitution reactions is set forth under the preparative procedure heading.

Runs 1 and Control A

Run 1 details a specific procedure for preparing hydrophobe substituted, cationic polysaccharides of this invention. The procedure involves adding $HEC_{mid\ MW}$ (147 parts by weight) and acetone diluent (1000 parts by weight) to a reactor vessel equipped with a stirrer, nitrogen supply, condenser and addition funnels. The reactor is purged with nitrogen and sodium hydroxide catalyst (17.3 parts by weight) is added in aqueous solution. After stirring for 0.5 hours, an aqueous solution containing $C_{12}ACl$ (79 parts by weight) is added. The reaction mixture is heated to 55° C. and held for three hours, at which time glacial acetic acid (14.6 parts by weight) is added with an additional fifteen minutes of stirring. The reaction solids are collected by filtration, are washed repeatedly with aqueous acetone, and are dried to yield hydrophobe substituted, cationic polysaccharide product (167.9 grams). A blend of product is measured to contain 0.4% nitrogen, representing a CS of 0.074. A 2 wt.% solution of the product blend in water is clear and gel-free with a viscosity of 699 cps. The solution forms a high stable foam.

The preparation of the hydrophobe substituted, cationic polysaccharide product is summarized in Table I. Control A pertains to the etherified polysaccharide starting material.

Runs 2–6

Based on the general procedure in Run 1, varying amounts of quaternizing/alkylating agent react to produce hydrophobe substituted, cationic polysaccharides having various degrees of quaternization/alkylation, i.e. CS and HS, respectively, in Runs 2–6. The preparations are summarized in Table I.

Runs 7 and Control B

Based on the general procedure in Run 1, a relatively high molecular weight hydroxyethyl cellulose as polysaccharide starting material reacts to produce the hydrophobe substituted, cationic polysaccharide in Run 7. The preparation is summarized in Table I. Control B describes the etherified polysaccharide starting material.

Runs 8–25 and Control C

Based on the general procedure in Run 1, quaternizing agent free of hydrophobe, added in combination with the quaternizing/alkylation agent, reacts to produce hydrophobe substituted, cationic polysaccharides having CS greater than HS in Runs 8–25. As in the previous runs, polysaccharides of varying HS, CS, and HEC molecular weight are provided. The preparations are summarized in Table I. Control C describes a relatively low molecular weight hydroxyethyl cellulose starting material.

Runs 26–34

Based on the general procedure in Run 1, adding quaternizing agent after the combined quaternization/alkylation reaction provides hydrophobe substituted, cationic polysaccharides having CS greater than HS. In Example 26, representative of the additional step, after purging with nitrogen, an aqueous solution containing CTACl (14.0 parts by weight) is added to a reactor vessel containing a slurry of hydrophobe substituted, cationic polysaccharide (47.3 parts by weight) produced from an initial quaternizing/alkylating step, in isopropyl alcohol diluent (320 parts by weight), containing an aqueous solution of sodium hydroxide catalyst (5.3 parts by weight), and the solution is stirred for 0.5 hours. The mixture is reacted at 55° C. for one hour, followed by acidification with acetic acid (4.3 parts by weight). As in the previous runs, hydrophobe substituted, cationic polysaccharides are prepared having varying CS, HS and HEC starting material molecular weight. The combined preparations are summarized in Table I.

Runs Controls D-F

Based on the general procedure in Run 1, a quaternizing agent free of hydrophobe, in place of the quaternizing/alkylating agent, reacts to produce cationic polysaccharides in Controls D and E comparable to the hydrophobe substituted, cationic polysaccharides in the previous runs, but which are free of hydrophobe substitution. Control F pertains to an existing cationic polysaccharide comparable to the hydrophobe substituted, cationic polysaccharides of the previous runs, but which is free of hydrophobe substitution. The preparations are summarized in Table I.

Runs 35-39 and Controls G-H

Quaternization is achieved through two steps by (1) amination, followed by (2) quaternization using alkyl halide in Runs 35-39. Controls G and H pertain to the aminated polysaccharide intermediate prior to quaternization. In Run 35, as a representative procedure, a reactor vessel is charged with $HEC_{high\ MW}$ (209 parts by weight) having a viscosity of 386 cps, and tertiary butyl alcohol diluents (1000 parts by weight). The mixture is nitrogen purged and sodium hydroxide (37 parts by weight) is added as an aqueous solution, followed by 0.5 hours stirring. DACl (27.8 parts by weight) is added and the reaction proceeds at 60° C. for 2.5 hours, when hydrochloric acid (21.8 parts by weight) is added. The product solids are filtered, washed repeatedly to remove salts, and dried to provide an aminated polysaccharide, Control G, having 0.45% N and a viscosity of 307 cps. A portion of the aminated polysaccharide (40.0 parts by weight) is charged with ethanol diluent (344 parts by weight) to a one liter reactor vessel under a nitrogen purge. $C_{12}Br$ (4.7 parts by weight) is added and the reaction carried out for four hours at 78° C. The product solids are filtered, rinsed three times with ethanol and dried. The preparations for all runs are summarized in Table I.

Runs 40-44 and Controls I-K

Based on the general procedures in Runs 1 and 34, different quaternizing/alkylating agents containing hydrophobes of various alkyl chain lengths react to produce hydrophobe substituted, cationic polysaccharides in Runs 40-44. Controls I-K pertain to alkyl or aryl substituted, cationic polysaccharides, respectively, in which the alkyl or aryl substituent, i.e. n-hexyl or benzyl, do not provide a polysaccharide having sufficient hydrophobicity to be a hydrophobe substituted, cationic polysaccharide of this invention. The preparations for all runs are summarized in Table I.

Runs 45 and Control L

Based on the general procedure in Run 1, hydrophobe substituted polysaccharide starting material, HSHEC, reacts with CTACl alkyating agent to produce hydrophobe substituted, cationic polysaccharide of this invention in Run 45. Control L pertains to the hydrophobe substituted polysaccharide starting material as disclosed in U.S. Pat. No. 4,228,277 (Landoll I) as discussed previously.

Runs 46-50 and Controls M-R

Based on the general procedure in Run 1, a variety of cellulosic ethers as polysaccharide starting material react with quaternizing or quaternizing/alkylating agents to produce hydrophobe substituted, cationic polysaccharides in Runs 46-50. Controls M-P pertain to various etherified polysaccharide starting materials. Controls Q and R are based on the general procedures in Run 1 wherein a quaternizing agent free of hydrophobes, in place of the quaternizing/alkylating agent, reacts to produce polysaccharides corresponding to the hydrophobe substituted, cationic hydroxypropyl methyl cellulose of Run 49 but which are free of hydrophobe substituents. The preparations for all runs are summarized in Table I.

Runs 51-52

Based on the general procedure in Run 1, non-cellulosic polysaccharides react to produce hydrophobe substituted, cationic polysaccharides in Runs 51-52. The preparations are summarized in Table I.

Runs 53-54

Glycidol reacts with cellulosic starting material, as described in German Patent Application Publication No. 3,301,667 (Engelskirchen et al.), followed by quaternization/alkylation based on the general procedure in Run 1, to produce hydrophobe substituted, cationic polysaccharide in Run 53. Based on the general procedure in Run 1, etherifying agent, ethylene oxide, added after quaternization/alkylation, reacts to produce additionally etherified, hydrophobe substituted, cationic polysaccharide in Run 54. Both preparations are summarized in Table I.

TABLE I

HYDROPHOBE SUBSTITUTED AND CONTROL POLYSACCHARIDE SYNTHESIS

| Run | Polysaccharide Starting Material | Etherification Agent | Quaternizing Agent | Alkylating Agent | Preparative Procedure[a] |
|---|---|---|---|---|---|
| A | $HEC_{mid\ MW}$ | [EO][b] | None | None | [E][b] |
| 1 | $HEC_{mid\ MW}$ | [EO][b] | —[c] | $C_{12}ACl$ | [E][b]; Q/A |
| 2 | $HEC_{mid\ MW}$ | [EO][b] | —[c] | $C_{12}ACl$ | [E][b]; Q/A |
| 3 | $HEC_{mid\ MW}$ | [EO][b] | —[c] | $C_{12}ACl$ | [E][b]; Q/A |
| 4 | $HEC_{mid\ MW}$ | [EO][b] | —[c] | $C_{12}ACl$ | [E][b]; Q/A |
| 5 | $HEC_{mid\ MW}$ | [EO][b] | —[c] | $C_{12}ACl$ | [E][b]; Q/A |
| 6 | $HEC_{mid\ MW}$ | [EO][b] | —[c] | $C_{12}ACl$ | [E][b]; Q/A |
| B | $HEC_{high\ MW}$ | [EO][b] | None | None | [E][b] |
| 7 | $HEC_{high\ MW}$ | [EO][b] | —[c] | $C_{12}ACl$ | [E][b]; Q/A |
| C | $HEC_{low\ MW}$ | [EO][b] | None | None | [E][b] |
| 8 | $HEC_{low\ MW}$ | [EO][b] | CTACl | $C_{12}ACl$ | [E][b]; Q/A + Q |

TABLE I-continued
HYDROPHOBE SUBSTITUTED AND CONTROL POLYSACCHARIDE SYNTHESIS

| Run | Polysaccharide Starting Material | Etherification Agent | Quaternizing Agent | Alkylating Agent | Preparative Procedure[a] |
|---|---|---|---|---|---|
| 9 | $HEC_{low\ MW}$ | $[EO]^b$ | CTACl | $C_{12}ACl$ | $[E]^b$; Q/A + Q |
| 10 | $HEC_{low\ MW}$ | $[EO]^b$ | CTACl | $C_{12}ACl$ | $[E]^b$; Q/A + Q |
| 11 | $HEC_{low\ MW}$ | $[EO]^b$ | CTACl | $C_{12}ACl$ | $[E]^b$; Q/A + Q |
| 12 | $HEC_{mid\ MW}$ | $[EO]^b$ | CTACl | $C_{12}ACl$ | $[E]^b$; Q/A + Q |
| 13 | $HEC_{mid\ MW}$ | $[EO]^b$ | CTACl | $C_{12}ACl$ | $[E]^b$; Q/A + Q |
| 14 | $HEC_{mid\ MW}$ | $[EO]^b$ | CTACl | $C_{12}ACl$ | $[E]^b$; Q/A + Q |
| 15 | $HEC_{high\ MW}$ | $[EO]^b$ | CTACl | $C_{12}ACl$ | $[E]^b$; Q/A + Q |
| 16 | $HEC_{high\ MW}$ | $[EO]^b$ | CTACl | $C_{12}ACl$ | $[E]^b$; Q/A + Q |
| 17 | $HEC_{high\ MW}$ | $[EO]^b$ | CTACl | $C_{12}ACl$ | $[E]^b$; Q/A + Q |
| 18 | $HEC_{high\ MW}$ | $[EO]^b$ | CTACl | $C_{12}ACl$ | $[E]^b$; Q/A + Q |
| 19 | $HEC_{high\ MW}$ | $[EO]^b$ | CTACl | $C_{12}ACl$ | $[E]^b$; Q/A + Q |
| 20 | $HEC_{high\ MW}$ | $[EO]^b$ | CTACl | $C_{12}ACl$ | $[E]^b$; Q/A + Q |
| 21 | $HEC_{high\ MW}$ | $[EO]^b$ | CTACl | $C_{12}ACl$ | $[E]^b$; Q/A + Q |
| 22 | $HEC_{high\ MW}$ | $[EO]^b$ | CTACl | $C_{12}ACl$ | $[E]^b$; Q/A + Q |
| 23 | $HEC_{high\ MW}$ | $[EO]^b$ | CTACl | $C_{12}ACl$ | $[E]^b$; Q/A + Q |
| 24 | $HEC_{high\ MW}$ | $[EO]^b$ | CTACl | $C_{12}ACl$ | $[E]^b$; Q/A + Q |
| 25 | $HEC_{mid\ MW}$ | $[EO]^b$ | CTEACl | $C_{12}ACl$ | $[E]^b$; Q/A + Q |
| 26 | $HEC_{low\ MW}$ | $[EO]^b$ | CTACl | $C_{12}ACl$ | $[E]^b$; Q/A + Q; Q |
| 27 | $HEC_{low\ MW}$ | $[EO]^b$ | CTACl | $C_{12}ACl$ | $[E]^b$; Q/A + Q; Q |
| 28 | $HEC_{mid\ MW}$ | $[EO]^b$ | CTACl | $C_{12}ACl$ | $[E]^b$; Q/A + Q; Q |
| 29 | $HEC_{mid\ MW}$ | $[EO]^b$ | CTACl | $C_{12}ACl$ | $[E]^b$; Q/A + Q; Q |
| 30 | $HEC_{high\ MW}$ | $[EO]^b$ | CTACl | $C_{12}ACl$ | $[E]^b$; Q/A + Q; Q |
| 31 | $HEC_{high\ MW}$ | $[EO]^b$ | CTACl | $C_{12}ACl$ | $[E]^b$; Q/A + Q; Q |
| 32 | $HEC_{high\ MW}$ | $[EO]^b$ | CTACl | $C_{12}ACl$ | $[E]^b$; Q/A + Q; Q |
| 33 | $HEC_{high\ MW}$ | $[EO]^b$ | CTACl | $C_{12}ACl$ | $[E]^b$; Q/A + Q; Q |
| 34 | $HEC_{high\ MW}$ | $[EO]^b$ | CTACl | $C_{12}ACl$ | $[E]^b$; Q/A + Q; Q |
| D | $HEC_{mid\ MW}$ | $[EO]^b$ | CTACl | None | $[E]^b$; Q |
| E | $HEC_{mid\ MW}$ | $[EO]^b$ | CTACl | None | $[E]^b$; Q |
| F | $HEC_{high\ MW}$ | $[EO]^b$ | $[CTACl]^b$ | None | $[E]^b$; $[Q]^b$ |
| G | $HEC_{high\ MW}$ | $[EO]^b$ | $DACl^d$ | None | $[E]^b$; Am |
| 35 | $HEC_{high\ MW}$ | $[EO]^b$ | $DACl^d$ | $C_{12}Br^c$ | $[E]^b$; AM; Q/A |
| H | $HEC_{high\ MW}$ | $[EO]^b$ | $DACl^d$ | None | $[E]^b$; Am |
| 36 | $HEC_{high\ MW}$ | $[EO]^b$ | $DACl^d$ | $C_{12}Br^c$ | $[E]^b$; Am; Q/A |
| 37 | $HEC_{high\ MW}$ | $[EO]^b$ | $DACl^d$ | $C_{12}Br^c$ | $[E]^b$; Am; Q/A |
| 38 | $HEC_{high\ MW}$ | $[EO]^b$ | $DACl^d$ | $C_{12}Br^c$ | $[E]^b$; Am; Q/A |
| 39 | $HEC_{high\ MW}$ | $[EO]^b$ | $DACl^d$ | $C_{12}Br^c$ | $[E]^b$; Am; Q/A |
| I | $HEC_{high\ MW}$ | $[EO]^b$ | $DACl^d$ | $C_6Br^c$ | $[E]^b$; Am; Q/A |
| J | $HEC_{mid\ MW}$ | $[EO]^b$ | —$^c$ | CDBACl | $[E]^b$; Q/A |
| K | $HEC_{mid\ MW}$ | $[EO]^b$ | —$^c$ | CDBACl | $[E]^b$; Q/A |
| 40 | $HEC_{mid\ MW}$ | $[EO]^b$ | —$^c$ | $C_8ACl^e$ | $[E]^b$; Q/A |
| 41 | $HEC_{high\ MW}$ | $[EO]^b$ | $DACl^d$ | $C_{10}Br^c$ | $[E]^b$; $Am^d$; Q/A |
| 42 | $HEC_{mid\ MW}$ | $[EO]^b$ | —$^c$ | $C_{10}ACl^e$ | $[E]^b$; Q/A |
| 43 | $HEC_{mid\ MW}$ | $[EO]^b$ | —$^c$ | $C_{12}ACl^e$ | $[E]^b$; Q/A |
| 44 | $HEC_{mid\ MW}$ | $[EO]^b$ | —$^c$ | $C_{18}ACl$ | $[E]^b$; Q/A |
| L | HSHEC | $[EO]^b$ | None | $[C_x]^f$ | $[E]^b$; $[A]^b$ |
| 45 | HSHEC | $[EO]^b$ | CTACl | $[C_x]^f$ | $[E]^b$; $[A]^b$; Q |
| M | HEHPC | $[EO,PO]^b$ | None | None | $[E]^b$ |
| 46 | HEHPC | $[EO,PO]^b$ | —$^c$ | $C_{12}ACl$ | $[E]^b$; Q/A |
| N | Cell | PO | None | None | E |
| 47 | Cell | PO | —$^c$ | $C_{12}ACl$ | E; Q/A |
| O | MC | $[MCl]^b$ | None | None | $[E]^b$ |
| 48 | MC | $[MCl]^b$ | —$^c$ | $C_{12}ACl$ | $[E]^b$; Q/A |
| P | HPMC | $[MCl,PO]^b$ | None | None | $[E]^b$ |
| Q | HPMC | $[MCl,PO]^b$ | CTACl | None | $[E]^b$; Q |
| R | HPMC | $[MCl,PO]^b$ | CTACl | None | $[E]^b$; Q |
| 49 | HPMC | $[MCl,PO]^b$ | —$^c$ | $C_{12}ACl$ | $[E]^b$; Q/A |
| 50 | CMC | $[ClAc^-Na^+]$ | —$^c$ | $C_{12}ACl$ | $[E]^b$; Q/A |
| 51 | Alginate | None | —$^c$ | $C_{12}ACl$ | Q/A |
| 52 | Chitosan | EO | —$^c$ | $C_{12}ACl$ | E; Q/A |
| 53 | Cell | Gly | —$^c$ | $C_{12}ACl$ | E; Q/A |
| 54 | $HEC_{mid\ MW}$ | $[EO]^b$, EO | —$^c$ | $C_{12}ACl$ | $[E]^b$; Q/A; E |

[a]Agents added sequentially as shown in steps separated by semicolons using the abbreviations:
A - alkylating
Am - aminating
E - etherifying
Q - quaternizing
Q/A - combined quaternizing and alkylating agent with a plus sign ("+") indicating combined use in one step.
[b]—Bracketed information indicates previously substituted starting material.
[c]—Quaternization combined in alkylation.
[d]—Aminating agent only, in two-step quaternization consisting of (1) amination followed by (2) quaternization during alkylation.
[e]—Prepared by reacting corresponding dimethylalkylamine with epichlorohydrin and gaseous HCl.
[f]—Long chain alkyl group contained in starting material.

EXAMPLE 2

Polysaccharide Properties

Properties of aqueous solutions containing various hydrophobe substituted or control, cationic or nonionic polysaccharides as set forth in Example 1, using the previously prescribed procedures, with regard to viscosity, CS, HS, foaming and surface pressure properties, are set forth in Table II. The foaming values designate the volume of foam, in milliliters (ml), provided initially following agitation ($\phi_o$), after one hour ($\phi_1$), after 3 hours ($\phi_3$) and after 24 hours ($\phi_{24}$). Foam retention after 24 hours is the most significant in measuring the foam retention capacity of surfactive molecules in aqueous solution. Measurements of surface pressure ($\pi$) and compressed surface pressure ($\pi_c$) are provided by surface analysis, as described previously.

TABLE II

PROPERTIES OF VARIOUS HYDROPHOBE SUBSTITUTED AND CONTROL POLYSACCHARIDES[a]

| Run No. | Viscosity η(cps) | CS | HS | Foaming (ml) $\phi_0$ $\phi_1$ $\phi_3$ | $\phi_{24}$ | Surface Pressure (dynes/cm) $\pi_c$ | $\pi_3$ | $\pi_0$ |
|---|---|---|---|---|---|---|---|---|
| A | 115 | 0 | — | — — — | — | — | — | — |
| 1 | 663 | 0.074 | 0.074 | 30 27 25 | 16 | 19.3 | 12.7 | 8.2 |
| 2 | 250 | 0.074 | 0.074 | 25 21 19 | 14 | 19.6 | 12.5 | 8.1 |
| 3 | 3,313 | 0.105 | 0.105 | — — — | — | — | — | — |
| 4 | 125 | 0.036 | 0.036 | 24 15 10 | 4 | 16.5 | 9.8 | 5.5 |
| 5 | 739 | 0.075 | 0.075 | — — — | — | — | — | — |
| 6 | 517 | 0.074 | 0.074 | — — — | — | — | — | — |
| B | 490 | 0 | 0 | 17 0 0 | 0 | 9.6 | 7.3 | 5.2 |
| 7 | 7,913 | 0.093 | 0.093 | — — — | — | — | — | — |
| C | 23 | 0 | 0 | — — — | — | — | — | — |
| 8 | 22 | 0.028 | 0.017 | 32 22 17 | 4 | 14.3 | 8.4 | 5.5 |
| 9 | 55 | 0.088 | 0.052 | 33 27 25 | 10 | 18.6 | 12.5 | 5.2 |
| 10 | 275 | 0.135 | 0.080 | 38 26 17 | 7 | 21.0 | 13.2 | 3.9 |
| 11 | 46 | 0.099 | 0.059 | — — — | — | — | — | — |
| 12 | 534 | 0.096 | 0.057 | 30 24 22 | 21 | 18.4 | 12.0 | 2.7 |
| 13 | 2,300 | 0.124 | 0.074 | 18 17 16 | 9 | 18.4 | 11.2 | 2.7 |
| 14 | 1,860 | 0.141 | 0.084 | 19 18 17 | 13 | 16.9 | 10.6 | 3.0 |
| 15 | 825 | 0.040 | 0.024 | 24 12 11 | 4 | 7.8 | 4.0 | 0.1 |
| 16 | 645 | 0.027 | 0.016 | 25 18 15 | 4 | 13.1 | 8.3 | 5.1 |
| 17 | 2,280 | 0.080 | 0.048 | 18 15 11 | 2 | 11.8 | 8.0 | 4.7 |
| 18 | 1,700 | 0.091 | 0.054 | 25 20 20 | 17 | 16.5 | 10.3 | 4.4 |
| 19 | 492 | 0.027 | 0.016 | 15 13 10 | 5 | 11.3 | 8.0 | 5.0 |
| 20 | 1,146 | 0.096 | 0.057 | 36 20 20 | 20 | 20.3 | 11.0 | 4.6 |
| 21 | 10,600 | 0.158 | 0.094 | 22 20 18 | 16 | 24.3 | 12.0 | 1.3 |
| 22 | 4,400 | 0.074 | 0.070 | 22 20 20 | 20 | 18.5 | 12.0 | 3.2 |
| 23 | 17,500 | 0.119 | 0.112 | 24 20 20 | 20 | 25.0 | 11.9 | 0.3 |
| 24 | 506,000 | 0.168 | 0.159 | 20 19 19 | 19 | 22.3 | 12.8 | 0.7 |
| 26 | 23 | 0.338 | 0.052 | 16 13 10 | 4 | 8.3 | 4.9 | 0.2 |
| 27 | 60 | 0.310 | 0.080 | 15 12 8 | 3 | 12.8 | 6.9 | 0.6 |
| 28 | 578 | 0.339 | 0.084 | 24 23 17 | 5 | 10.6 | 5.3 | 0.5 |
| 29 | 253 | 0.308 | 0.057 | 14 12 11 | 4 | 7.8 | 4.0 | 0.1 |
| 30 | 578 | 0.315 | 0.054 | 14 13 10 | 2 | 11.4 | 5.8 | 0.4 |
| 31 | 238 | 0.295 | 0.016 | 13 11 7 | 2 | 6.7 | 4.0 | 0.6 |
| 32 | 24,000 | 0.325 | 0.159 | 21 20 20 | 15 | 12.4 | 6.4 | 0.3 |
| 33 | 3,100 | 0.340 | 0.112 | 21 20 19 | 15 | 10.6 | 5.1 | 0.1 |
| 34 | 3,100 | 0.413 | 0.094 | 16 16 15 | 14 | 9.7 | 3.4 | 0.2 |
| D | 73 | 0.079 | 0 | — — — | — | — | — | — |
| E | 65 | 0.193 | 0 | 15 0 0 | 0 | 9.2 | 7.0 | 5.0 |
| F | 456 | 0.38 | 0 | 10 0 0 | 0 | 8.3 | 4.3 | 0.6 |
| 35 | 493 | 0.016 | 0.016 | 28 16 13 | 2 | 12.4 | 7.8 | 4.5 |
| G | 307 | 0 20%[b] | 0 | 16 3 0 | 0 | 8.6 | 6.3 | 3.7 |
| H | 372 | 0 | 0 | 18 3 0 | 0 | 8.0 | 6.1 | 3.4 |
| 36 | 412 | 0.008 20%[b] | 0.008 | 20 8 4 | 0 | 9.5 | 6.8 | 4.3 |
| 39 | 3,953 | 0.028 32.2%[b] | 0.028 | 22 13 13 | 10 | 20.8 | 10.0 | 4.9 |
| J | 50 | 0.21 | 0 | 16 0 0 | 0 | — | — | — |
| K | 42 | 0.29 | 0 | 14 0 0 | 0 | — | — | — |
| 40 | 105 | 0.096 | 0.096 | 20 4 1 | 0 | 11.5 | 8.8 | 3.5 |
| 42 | 90 | 0.113 | 0.113 | 29 22 20 | 7 | 21.8 | 13.6 | 7.1 |
| 43 | 399 | 0.089 | 0.089 | 27 23 20 | 3 | 20.5 | 14.4 | 5.9 |
| 44 | 11,792 | 0.026 | 0.026 | — — — | — | — | — | — |
| L | 2,210 | 0 | —[c] | — — — | — | — | — | — |
| 45 | 2,277 | 0.063 | —[c] | — — — | — | — | — | — |
| M | 54 | 0 | 0 | 16 5 4 | 0 | 29.8 | 16.7 | 13.9 |
| 46 | 205 | 0.067 | 0.067 | 24 18 16 | 5 | 27.4 | 18.8 | 11.6 |
| O | 392 | 0 | 0 | 25 7 4 | 0 | 30.5 | 23.3 | 16.3 |
| 48 | 12,800 | 0.059 | 0.059 | 20 19 18 | 17 | 32.7 | 24.6 | 14.1 |
| P | 86 | 0 | 0 | 20 7 3 | 0 | 29.1 | 22.8 | 18.0 |
| Q | 105 | 0.026 | 0 | 28 15 4 | 0 | — | — | — |
| R | 132 | 0.014 | 0 | 28 15 7 | 1 | — | — | — |
| 49 | 32,700 | 0.076 | 0.076 | 27 18 18 | 18 | 33.9 | 27.3 | 20.6 |

[a]Dashes indicate no data available.
[b]Only designated percentage of amine substituent quaternized.
[c]Information not available for starting material.

EXAMPLE 3

Comparative Analysis

In these comparisons, the extent of enhancement of viscosity, foaming and surface pressure is analyzed by comparing hydrophobe substituted, cationic polysaccharides with similar or corresponding polysaccharides free of hydrophobes. The enhancement in viscosity and surface pressure is present in terms of the percentage increase in values provided by the hydrophobe substituted, cationic polysaccharides as compared to the values provided by the control polysaccharides. The foaming enhancement is presented in terms of the volume of foam remaining 24 hours after agitation of aqueous solutions containing the hydrophobe substituted, cationic polysaccharides as compared to aqueous solutions of the control polysaccharides which generally contained no foam.

It is also demonstrated that enhanced viscosity, foaming and preferably surface pressure increases are generally provided for aqueous solutions containing a wide variety of hydrophobe substituted, cationic polysaccharides varying in: polysaccharide type or molecular weight; extent of quaternization; extent of alkylation; alkyl chain length of the hydrophobe; and preparative procedure, whether by combined or sequential quaternizations/alkylation.

The comparative data is presented in Table III.

TABLE III

COMPARATIVE ANALYSIS OF HYDROPHOBE SUBSTITUTED VERSUS CONTROL POLYSACCHARIDES

| Compared Polysaccharides Run | Control | Polysaccharide Type | Hydrophobe v Control | Enhancement Viscosity η | Foaming $\phi^a$ | Surface Pressure $\pi_c$ | $\pi_3$ |
|---|---|---|---|---|---|---|---|
| 1 | E | HEC$_{mid\ MW}$ | C$_{12}$v C$_1$ | 1,080% | 0→16 | 210% | 181% |
| 2 | | | C$_{12}$v C$_1$ | 385% | 0→14 | 213% | 179% |
| 4 | | | C$_{12}$v C$_1$ | 190% | 0→4 | 179% | 140% |

TABLE III-continued

COMPARATIVE ANALYSIS OF HYDROPHOBE
SUBSTITUTED VERSUS CONTROL POLYSACCHARIDES

| Run | Compared Polysaccharides Control | Polysaccharide Type | Hydrophobe v Control | Enhancement Viscosity $\eta$ | Foaming $\phi^a$ | Surface Pressure $\pi_c$ | $\pi_3$ |
|---|---|---|---|---|---|---|---|
| 12 | | | $C_{12}v\ C_1$ | 820% | 0→21 | 200% | 171% |
| 13 | | | $C_{12}v\ C_1$ | 3,540% | 0→9 | 200% | 160% |
| 14 | | | $C_{12}v\ C_1$ | 2,860% | 0→13 | 184% | 151% |
| 28 | | | $C_{12}v\ C_1$ | 890% | 0→5 | 115% | 76% |
| 29 | | | $C_{12}v\ C_1$ | 389% | 0→4 | 85% | 57% |
| 40 | | | $C_{18}v\ C_1$ | 160% | 0→0 | 125% | 126% |
| 42 | | | $C_{10}v\ C_1$ | 140% | 0→7 | 237% | 194% |
| 43 | | | $C_{12}v\ C_1$ | 610% | 0→3 | 223% | 206% |
| 15 | F | $HEC_{high\ MW}$ | $C_{12}v\ C_1$ | 55% | 0→4 | 94% | 93% |
| 16 | | | $C_{12}v\ C_1$ | 142% | 0→4 | 158% | 193% |
| 17 | | | $C_{12}v\ C_1$ | 500% | 0→2 | 142% | 186% |
| 18 | | | $C_{12}v\ C_1$ | 370% | 0→17 | 199% | 240% |
| 19 | | | $C_{12}v\ C_1$ | 107% | 0→5 | 136% | 186% |
| 20 | | | $C_{12}v\ C_1$ | 251% | 0→20 | 245% | 256% |
| 21 | | | $C_{12}v\ C_1$ | 2,300% | 0→16 | 293% | 279% |
| 22 | | | $C_{12}v\ C_1$ | 965% | 0→20 | 223% | 279% |
| 23 | | | $C_{12}v\ C_1$ | 3,837% | 0→20 | 301% | 277% |
| 24 | | | $C_{12}v\ C_1$ | 110,960% | 0→19 | 269% | 298% |
| 30 | | | $C_{12}v\ C_1$ | 127% | 0→2 | 137% | 135% |
| 31 | | | $C_{12}v\ C_1$ | 52% | 0→2 | 81% | 93% |
| 32 | | | $C_{12}v\ C_1$ | 5,260% | 0→15 | 149% | 149% |
| 33 | F | $HEC_{high\ MW}$ | $C_{12}v\ C_1$ | 680% | 0→15 | 128% | 119% |
| 34 | | | $C_{12}v\ C_1$ | 680% | 0→14 | 117% | 79% |
| 35 | G | $HEC_{high\ MW}$ | $C_{12}v\ C_1{}^b$ | 161% | 0→2 | 144% | 124% |
| 8 | C | $HEC_{low\ MW}$ | $C_{12}v$—$^c$ | 96% | — | — | — |
| 9 | | | $C_{12}v$—$^c$ | 239% | — | — | — |
| 10 | | | $C_{12}v$—$^c$ | 1,200% | — | — | — |
| 11 | | | $C_{12}v$—$^c$ | 200% | — | — | — |
| 26 | | | $C_{12}v$—$^c$ | 100% | — | — | — |
| 27 | | | $C_{12}v$—$^c$ | 261% | — | — | — |
| 46 | M | HEHPC | $C_{12}v$ —$^c$ | 380% | — | — | — |
| 48 | O | MC | $C_{12}v$—$^c$ | 3,260% | 0→17 | 107% | 105% |
| 49 | P-R | HPMC | $C_{12}v$—,$^cC_1$ | 24,770-38,000% | 0→1→18 | 116% | 120% |

$^a$Foam remaining after 24 hours (in ml) for solution with hydrophobe substituted, cationic polysaccharide listed on right versus control foam listed on left.
$^b$Comparison between hydrophobe substituted, cationic polysaccharide and corresponding aminated polysaccharide intermediate prior to quaternization.
$^c$Comparison between hydrophobe substituted, cationic polysaccharide and corresponding polysaccharide starting material free of quaterization and hydrophobe substitution.

EXAMPLE 4

Hair Treatment Evaluation

In this example, various hydrophobe substituted, cationic polysaccharides are evaluated for treating hair using the previously described procedure. Aqueous solutions containing the hydrophobe substituted, cationic polysaccharides in Example 1 in general provide significant utility including substantivity and curl retention, with or without added surfactant (using 10 wt. % sodium dodecyl sulfate or triethanolamine dodecyl sulfate).

EXAMPLE 5

Hand Lotion Evaluation

In this example, oil-in-water emulsions representative of typical hand lotion compositions, are prepared using the following formulations:

| | Wt. % |
|---|---|
| Oil Phase | |
| Mineral Oil | 2.40 |
| Isopropyl myristate | 2.40 |
| Stearic acid | 2.90 |
| Lanolin alcohol | 0.50 |
| Cetyl alcohol | 0.40 |
| Glycerol monostearate | 1.00 |

-continued

| | Wt. % |
|---|---|
| Propylparaben | 0.05 |
| Water Phase | |
| Triethanolamine | 0.95 |
| Propylene glycol | 4.80 |
| Methylparaben | 0.10 |
| Polysaccharide$^a$ | 0–1.0$^a$ |
| Water | Balance |

$^a$The type and amount of polysaccharide are given in Table IV.

The emulsion is prepared by heating the oil phase to 70° C. In a separate container polysaccharide is dissolved in water, the remaining water phase ingredients are then added and the solution is heated to 70° C. The oil and water phases are combined while stirring vigorously. Stirring is continued while the temperature is reduced to 35 ° C. or less.

Samples of lotions containing varying amounts and types of polysaccharides as in Table IV are placed in an oven at 50° C. and the stability of the samples are measured based on resistance to phase separation. The results, set forth in Table IV, demonstrate that emulsions containing cationic polysaccharide free of hydrophobe substitution exhibit phase separation, i.e., have reduced storage stability. In contrast, corresponding emulsions containing hydrophobe substituted, cationic polysaccharides of this invention provide stable emulsions without any phase separation for over 30 days.

TABLE IV
STORAGE STABILITY OF EMULSIONS CONTAINING HYDROPHOBE SUBSTITUTED OR CONTROL CATIONIC POLYSACCHARIDES

| Sample No. | Polysaccharide Type | Amount (wt. %) | Phase separation |
|---|---|---|---|
| 1 | None | 0 | None after 30 days |
| 2 | Run F[a] | 0.5 | In 7 days |
| 3 | Run F[a] | 1.0 | In 3 days |
| 4 | HSCP I[b] | 0.5 | None after 30 days |
| 5 | HSCP I[b] | 1.0 | None after 30 days |
| 6 | HSCP II[b] | 0.5 | None after 30 days |
| 7 | HSCP II[b] | 1.0 | None after 30 days |
| 8 | HSCP III[b] | 0.5 | None after 30 days |
| 9 | HSCP III[b] | 1.0 | None after 30 days |

[a] Quaternary nitrogen-containing hydroxyethyl cellulose described in Run F in Tables I and II.
[b] Hydrophobe substituted cationic polysaccharide which is $C_{12}$ alkyl substituted, quaternary nitrogen-containing hydroxyethyl cellulose, prepared following the general procedures in Run 1 of Example 1 having the following CS, HS and viscosity:

| Samples | Type | CS | HS | Viscosity (cps) |
|---|---|---|---|---|
| 4 + 5 | HSCP I | 0.091 | 0.091 | 411 |
| 6 + 7 | HSCP II | 0.069 | 0.069 | 490 |
| 8 + 9 | HSCP III | 0.055 | 0.055 | 200 |

EXAMPLE 6

Viscosity Change Due to Ionic Content

This example demonstrates the effect that ionic concentration, such as through salt addition, has on the viscosity of aqueous solutions containing hydrophobe substituted, cationic polysaccharides as compared to cationic polysaccharides free of hydrophobe substitution. Under normal circumstances the presence of additional ionic species, such as provided by salt addition, in aqueous solutions of ionic polysaccharides, would be expected to cause a collapsing of the polymer chain, thereby reducing its hydrodynamic volume and, consequently, the solution viscosity. The effect of adding salt in varying amounts on the viscosity of aqueous solutions of polysaccharides is presented in Table V. Preferred hydrophobe substituted, cationic polysaccharides of this invention provide increased viscosities to aqueous solutions of the polysaccharides upon salt addition, in contrast to polysaccharides free of hydrophobes which provide a reduction in aqueous solution viscosities with salt addition. The hydrophobe substituted polysaccharide produced in Run #40, having a hydrophobe containing alkyl group of 8 carbon atoms, does not provide increased viscosity upon salt addition, indicating that either additional hydrophobe substitution is required or that hydrophobes containing alkyl groups of greater than 8 carbon atoms may be required to provide this property.

TABLE V
VISCOSITY VERSUS SALT CONCENTRATION

| Polysaccharide Run | Polysaccharide Type | Hydrophobe (v Control) | % Salt Concentration[a] | Viscosity |
|---|---|---|---|---|
| 5 | HEC$_{mid\ MW}$ | $C_{12}$ | 1.0 | 393 |
| | | | 1.7 | 458 |
| | | | 2.2 | 517 |
| | | | 2.4 | 739 |
| | | | 4.8 | 1,140 |
| | | | 6.4 | 1,443 |
| | | | 8.7 | 1,840 |
| | | | 11.2 | 2,160 |
| | | | 13.0 | 2,127 |
| 6 | HEC$_{mid\ MW}$ | $C_{12}$ | 0.8 | 332 |
| | | | 1.7 | 430 |
| | | | 2.9 | 823 |
| | | | 4.2 | 1,081 |
| | | | 5.0 | 1,190 |
| | | | 6.2 | 1,237 |
| 40 | HEC$_{mid\ MW}$ | $C_8$ | 0.3 | 105 |
| | | | 3.4 | 83 |
| | | | 6.2 | 86 |
| | | | 8.6 | 83 |
| E | HEC$_{mid\ MW}$ | ($C_1$) | 1.9 | 75 |
| | | | 5.0 | 68 |
| | | | 7.5 | 65 |
| | | | 10.2 | 63 |
| F | HEC$_{high\ MW}$ | ($C_1$) | 2.9 | 456 |
| | | | 5.7 | 271 |
| | | | 8.5 | 283 |
| Q | HPMC | ($C_1$) | 0.9 | 105 |
| | | | 1.9 | 105 |
| | | | 4.3 | 84 |
| | | | 5.7 | 85 |
| | | | 9.3 | 63 |
| R | HPMC | ($C_1$) | 0.05 | 132 |
| | | | 0.2 | 110 |
| | | | 0.3 | 112 |
| | | | 1.2 | 118 |
| | | | 4.9 | 78 |

[a] % NaCl derived from ash data analysis given as contained salt on a dry polymer basis.

EXAMPLE 7

Water-Solubility Due to Cationization

This example compares the water-solubilities in aqueous solutions of hydrophobe substituted, cationic polysaccharides of this invention with substantially corresponding nonionic, hydrophobe substituted polysaccharide of the prior art, as described in U.S. Pat. No. 4,228,277 (Landoll I) as described previously. The comparison, based on the 2 wt.% Brookfield viscosities of various polysaccharides shown in Table VI, demonstrates the significantly enhanced water-solubility of hydrophobe substituted, cationic polysaccharides of this invention, based on solution viscosity, even at much higher hydrophobe substitution levels and for higher molecular weight polysaccharides as compared to nonionic hydrophobe substituted polysaccharides of the prior art.

TABLE VI
WATER SOLUBILITY OF CATIONIC v. NONIONIC HYDROPHOBE SUBSTITUTED POLYSACCHARIDES

| Run No. | HEC MW[a] | Hydrophobe Content Chain Length[b] | Weight % | Viscosity[c] |
|---|---|---|---|---|
| 2 | Mid[d] | $C_{12}$ | 6.4 | 3,313 |
| 22 | High[e] | $C_{12}$ | 7.1 | 17,500 |
| 23 | High[e] | $C_{12}$ | 9.6 | 506,000 |
| Prior | Low[g] | $C_{12}$ | 3.4 | Insoluble |

TABLE VI-continued
WATER SOLUBILITY OF CATIONIC v. NONIONIC HYDROPHOBE SUBSTITUTED POLYSACCHARIDES

| Run No. | HEC MW[a] | Chain Length[b] | Weight % | Viscosity[c] |
|---|---|---|---|---|
| Art[f] | | | | |

[a]Molecular weight of hydroxyethyl cellulose starting material.
[b]Number of carbon atom in hydrophobe alkyl group.
[c]Brookfield viscosity of 2 wt. % polysaccharide solution at 25° C.
[d]Starting material characterized by a 2 wt. to Brookfield viscosity at 25° C. of 115 cps.
[e]Starting material characterized by a 2 wt. to Brookfield viscosity at 25° C. of 490 cps.
[f]Example No. 4 of Table I described at column 3, line 63 of Landoll I patent.
[g]Starting material characterized at low molecular weight having an intrinsic viscosity of 1.5, and a 2% solution viscosity of 12 cps, as shown in the Control Example of Table I of the Landoll I patent.

What is claimed is:

1. A water-soluble, quaternary nitrogen-containing polysaccharide represented by the overall structural formula:

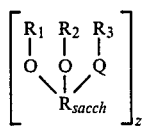

wherein:

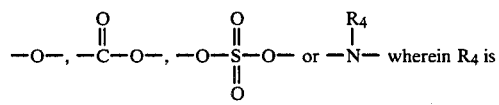

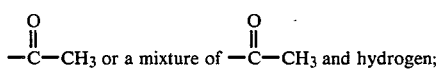

$R_{sacch}$ is the residue of a polysaccharide repeat unit;
z is from 50 to about 20,000; and
each $R_1$, $R_2$ and $R_3$ is individually represented by the substituent structural formula:

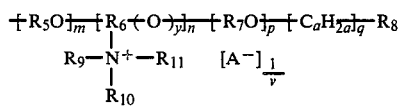

wherein:
A is an anion;
a is an integer of from 1 to about 3;
m is an integer of from 0 to about 6;
n is an integer of from 0 to about 3, provided that the level of cationic substitution, CS, defined by the average moles of quaternary nitrogen atoms per mole polysaccharide repeat unit is greater than 0;
p is an integer of from 0 to about 6;
q is 0 or 1;
each $R_5$ and $R_7$ is individually ethylene, a propylene or a hydroxypropylene;
$R_6$ is a di- or trivalent, branched or straight chain, saturated or unsaturated hydrocarbon having from 2 to about 4 carbon atoms, provided there are at least 2 carbon atoms between the nitrogen atom and any oxygen atom;

$R_8$ is hydrogen, hydroxyl, $R_h$, carboxyl or alkali metal or amine carboxylate, provided that when q is 0 then $R_8$ is hydrogen or $R_h$;

each $R_9$, $R_{10}$ and $R_{11}$ is individually $R_h$, alkyl, aryl, aralkyl, alkaryl, cycloalkyl, alkoxyaryl or alkoxyalkyl, having at least two carbon atoms separating the oxygen atom in the alkoxyaryl or alkoxyalkyl group from the nitrogen atom;

$R_h$ is a hydrophobic group containing an alkyl group having at least 8 carbon atoms;

v is equal to the valence of A;

y is 0 or 1, provided that when y is 0 then p and q are 0 and $R_8$ is hydrogen;

with the proviso that at least one $R_h$ group is present such that the extent of hydrophobic group substitution, HS, defined by the average moles of said hydrophobic groups per mole of polysaccharide repeat unit, is greater than 0 and is sufficient to provide for enhanced viscosification and foaming of aqueous solutions containing the polysaccharide.

2. The polysaccharide of claim 1 wherein:
Q is —O—;
$R_{sacch}$ is the residue of cellulose;
z is from about 250 to about 4,000;
A is chloride;
n is from 0 to about 2;
CS and HS are each individually from about 0.096 to about 0.113;
p is 0;
q is 0;
$R_5$ is ethylene;
$R_6$ is

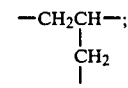

$R_8$ is hydrogen;
$R_9$ and $R_{10}$ are methyl;
$R_{11}$ is $R_h$;
$R_h$ is alkyl having from 8 to 10 carbon atoms;
v is 1; and
y is 1.

3. A water-soluble, quaternary nitrogen-containing polysaccharide represented by the overall structural formula:

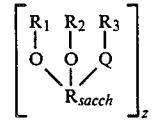

wherein:
Q is

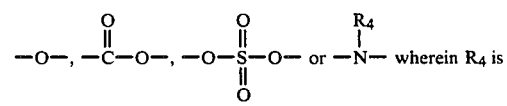

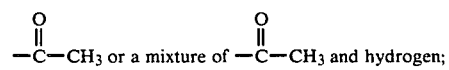

$R_{sacch}$ is the residue of a polysaccharide repeat unit;

z is from 50 to about 20,000; and each $R_1$, $R_2$ and $R_3$ is individually represented by the substituent structural formula:

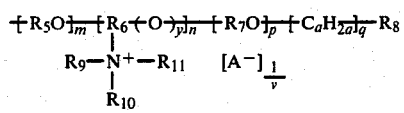

wherein:

A is an anion;

a is an integer of from 1 to about 3;

m is an integer of from 0 to about 6;

n is an integer of from 0 to about 3, provided that the level of cationic substitution, CS, defined by the average moles of quaternary nitrogen atoms per mole polysaccharide repeat unit is greater than 0;

p is an integer of from 0 to about 6;

q is 0 or 1;

each $R_5$ and $R_7$ is individually ethylene, a propylene or a hydroxypropylene;

$R_6$ is a di- or trivalent, branched or straight chain, saturated or unsaturated hydrocarbon having from 2 to about 4 carbon atoms, provided there are at least 2 carbon atoms between the nitrogen atom and any oxygen atom;

$R_8$ is hydrogen, hydroxyl, $R_h$, carboxyl or alkali metal or amine carboxylate, provided that when q is 0 then $R_8$ is hydrogen or $R_h$;

each $R_9$, $R_{10}$ and $R_{11}$ is individually $R_h$, alkyl, aryl, aralkyl, alkaryl, cycloalkyl, alkoxyaryl or alkoxyalkyl, having at least two carbon atoms separating the oxygen atom in the alkoxyaryl or alkoxyalkyl group from the nitrogen atom;

$R_h$ is a hydrophobic group containing a alkyl group having at least 8 carbon atoms;

v is equal to the valence of A;

y is 0 or 1, provided that when y is 0 then p and q are 0 and $R_8$ is hydrogen;

with the proviso that at least one $R_h$ is persent such that the extent of hydrophobic group substitution, HS, defined by the average moles of said hydrophobic groups per mole of polysaccharide repeat unit, is greater then 0; and wherein $R_h$ is present as (1) at least one $R_8$; (2) at least one $R_9$, $R_{10}$ or $R_{11}$ as a hydrophobic group containing an alkyll group having at least about 12 carbon atoms; or (3) both (1) and (2).

4. The polysaccharide of claim 3 wherein at least one $R_8$ is $R_h$.

5. The polysaccharide of claim 1 wherein said polysaccharide, when compared with a polysaccharide having essentially the same structure but which is free of said hydrophobic groups, provides significantly increased viscosity and foaming to aqueous solutions of the polysaccharide.

6. The polysaccharide of claim 5 which provides an aqueous solution viscosity, at a 2 weight % polysaccharide content, in excess of about 115% as compared with a polysaccharide having essentially the same structure but which is free of said hydrophobic groups.

7. The polysaccharide of claim 6 which provides said solution viscosity in excess of about 200% as compared with a polysaccharide having essentially the same structure but which is free of said hydrophobic groups.

8. The polysaccharide of claim 7 which provides said solution viscosity in excess of about 300% to about 100,000% as compared with a polysaccharide having essentially the same structure but which is free of said hydrophobic groups.

9. The polysaccharide of claim 3 wherein $R_{sacch}$ is the residue of cellulose, starch, chitosan, chitin, alginate, carrogeenan, natural gums or bio-derived polysaccharides.

10. The polysaccharide of claim 9 wherein $R_{sacch}$ is the residue of cellulose or cellulose ether.

11. The polysaccharide of claim 10 wherein said cellulose ether is hydroxyethyl cellulose, hydroxypropyl cellulose, methyl cellulose, hydroxypropyl methyl cellulose, ethyl cellulose or carboxymethyl cellulose.

12. The polysaccharide of claim 11 wherein said cellulose ether is hydroxyethyl cellulose.

13. The polysaccharide of claim 3 wherein $R_h$ contains an alkyl group having from about 12 to about 24 carbon atoms.

14. The polysaccharide of claim 13 wherein $R_h$ contains an alkyl group having from about 12 to about 18 carbon atoms.

15. The polysaccharide of claim 3 wherein:

Q is —O—;

$R_{sacch}$ is the residue of cellulose;

z is from about 100 to about 6,000;

A is chloride, bromide, iodide, sulfate, methyl sulfate, sulfonate, nitrate, phosphate or acetate;

the extent of the molar substitution, MS, which is the average number of moles of substituents in m+p+q per polysaccharide repeat unit, is greater than about 1.2;

n is from 0 to about 2;

CS and HS are each less than 1;

each $R_5$ and $R_7$ is individually ethylene or isopropylene;

$R_6$ is ethylene or

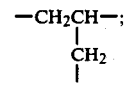

$R_8$ is hydrogen or $R_h$;

each $R_9$ and $R_{10}$ is individually alkyl having from 1 to about 3 carbon atoms;

$R_{11}$ is alkyl containing from 1 to about 3 carbon atoms or $R_h$;

$R_h$ contains an alkyl group having from about 12 to about 24 carbon atoms; and v is 1.

16. The polysaccharide of claim 15 wherein:

z is from about 250 to about 4000;

A is chloride;

n is 1;

CS and HS are each individually from about 0.01 to about 0.6;

p is 0;

MS is from about 1.2 to about 4.5;

$R_5$ is ethylene;

$R_6$ is

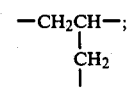

$R_9$ and $R_{10}$ are methyl;

$R_{11}$ is methyl or $R_h$;

$R_h$ is alkyl having from about 12 to about 18 carbon atoms; and y is 1.

17. An aqueous composition comprising water and an effective amount of the polysaccharide of claim 1.

18. The aqueous composition of claim 17 containing an effective viscosifying amount of added salt.

19. A hair or skin care composition comprising a solvent and an effective amount of the polysaccharide of claim 1.

20. A shampoo comprising an effective amount of hair or skin care composistion of claim 19.

21. An emulsion comprising oil, water and an effective amount of the polysaccharide of claim 1.

22. A hand lotion comprising an effective amount of oil-in-water emulsion of claim 21.

23. A cleaning composition comprising a cleanser and an effective amount of the polysaccharide of claim 1.

24. The polysaccharide of claim 3 wherein said polysaccharide is hydroxyethyl cellulose containing an amount of said hydrophobic groups sufficient to provide for enhanced viscosification, foaming and surface pressure of aqueous solutions containing the hydroxyethyl cellulose.

25. The hydroxyethyl cellulose of claim 24 wherein said hydroxyethyl cellulose, when compared with a hydroxyethyl cellulose having essentially the same structure but which is free of said hydrophobic groups, provides significantly increased viscosity, foaming and surface pressure differential to aqueous solutions of the hydroxyethyl cellulose.

26. The hydroxyethyl cellulose of claim 25 which provides:
(a) an aqueous solution viscosity, at a 2 wt. % hydroxyethyl cellulose content at 25° C., in excess of about 115%; and
(b) a surface pressure in aqueous solution at 25° C., in excess of about 110%;
as compared with a hydroxyethyl cellulose having essentially the same structure but which is free of said hydrophobic groups.

27. The hydroxyethyl cellulose of claim 26 which provides:
(a) said aqueous solution viscosity in excess of about 200%;
(b) said surface pressure in excess of about 120%;
as compared with a hydroxyethyl cellulose having essentially the same structure but which is free of said hydrophobic groups.

28. The hydroxyethyl cellulose of claim 27 which provides:
(a) said aqueous solution viscosity from about 300% to about 100,000%;
(b) said surface pressure from about 125% to about 300%;
as compared with a hydroxyethyl cellulose having essentially the same structure but which is free of said hydrophobic groups.

29. The hydroxyethyl cellulose of claim 12 wherein $R_h$ contains an alkyl group having from about 12 to about 24 carbon atoms.

30. The hydroxyethyl cellulose of claim 29 wherein $R_h$ contains an alkyl group having from about 12 to about 18 carbon atoms.

31. The hydroxyethyl cellulose of claim 12 wherein:
z is from about 100 to about 6,000;
A is chloride, bromide, iodide, sulfate, methyl sulfate, sulfonate, nitrate, phosphate or acetate;
the extent of molar substitution MS, which is the average number of moles of substituents in m+p per anhydroglucose repeat unit, is greater than about 1.2;
n is from 0 to about 2;
CS and HS are less that 1;
$R_6$ is ethylene or

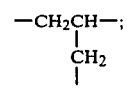

each $R_9$ and $R_{10}$ is individually alkyl having from 1 to about 3 carbon atoms;
$R_{11}$ is alkyl having from 1 to about 3 carbon atoms or $R_h$;
$R_h$ contains an alkyl group having from about 12 to about 24 carbon atoms; and
v is 1.

32. The hydroxyethyl cellulose of claim 31 wherein:
z is from about 250 to about 4,000;
A is chloride;
n is 1;
CS and HS are from about 0.02 to about 0.6;
p is 0;
MS is from about 1.2 to about 4.5;
$R_6$ is

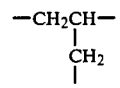

$R_8$ is hydrogen;
$R_9$ and $R_{10}$ are methyl;
$R_{11}$ is methyl or $R_h$;
$R_h$ is alkyl having from about 12 to about 18 carbon atoms; and
y is 1.

33. An aqueous composition for cosmetic and non-cosmetic applications, comprising water and an effective amount of the hydroxyethyl cellulose of claim 12.

34. The aqueous composition for cosmetic and non-cosmetic applications, of claim 33 containing an effective viscosifying amount of added salt.

35. A hair or skin care composition comprising a solvent and an effective amount of the hydroxyethyl cellulose of claim 12.

36. A shampoo comprising an effective amount of the hair or skin care composition of claim 35.

37. An emulsion for cosmetic and non-cosmetic applications, comprising oil, water and an effective amount of the hydroxyethyl cellulose of claim 12.

38. A hand lotion comprising an effective amount of the oil-in-water emulsion of claim 37.

39. A cleaning composition for cosmetic and non-cosmetic applications, comprising a cleanser and an effective amount of the hydroxyethyl cellulose of claim 12.

* * * * *

REEXAMINATION CERTIFICATE (1861st)//
United States Patent [19]
Brode, II et al.

[11] B1 4,663,159
[45] Certificate Issued Dec. 1, 1992

[54] HYDROPHOBE SUBSTITUTED, WATER-SOLUBLE CATIONIC POLYSACCHARIDES

[75] Inventors: George L. Brode, II, Bridgewater; Russell L. Kreeger, Somerville; Errol D. Goddard, Haworth; Frederick M. Merritt, II, Belle Mead, all of N.J.; David B. Braun, Ridgefield, Conn.

[73] Assignee: Union Carbide Corporation

Reexamination Request:
No. 90/002,084, Jul. 6, 1990

Reexamination Certificate for:
Patent No.: 4,663,159
Issued: May 5, 1987
Appl. No.: 697,241
Filed: Feb. 1, 1985

[51] Int. Cl.$^5$ .................... A61K 7/06; C08B 11/00
[52] U.S. Cl. .................... 424/70; 536/43; 536/90; 536/91; 514/844; 514/84.7
[58] Field of Search .................... 536/43, 90, 91; 514/844, 847; 424/70

[56] References Cited

U.S. PATENT DOCUMENTS

| | | | |
|---|---|---|---|
| 2,768,162 | 10/1956 | Evans | 260/231 |
| 3,472,840 | 10/1969 | Stone et al. | 536/43 |
| 3,498,912 | 3/1970 | Kieper et al. | 210/728 |
| 3,598,730 | 8/1971 | Nordgren | 210/54 |
| 3,931,148 | 1/1976 | Langdon | 260/210 |
| 4,001,394 | 1/1977 | Fogel et al. | 252/544 |
| 4,228,277 | 10/1980 | Landoll | 536/91 |
| 4,243,802 | 1/1981 | Landoll | 536/91 |

FOREIGN PATENT DOCUMENTS

71635 11/1976 Luxembourg.
1136842 12/1968 United Kingdom.

*Primary Examiner*—Johnnie R. Brown

[57] ABSTRACT

Water-soluble, cationic polysaccharides, including quaternary nitrogen-containing cellulose ethers, containing hydrophobic substitution, are substantially water-soluble; provide aqueous solutions having enhanced viscosity, foaming and preferably improved surface properties; and possess utility in personal care, emulsions and cleansers.

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-39 are cancelled.

* * * * *